United States Patent
Tsuzuki et al.

(10) Patent No.: US 10,434,042 B2
(45) Date of Patent: Oct. 8, 2019

(54) COMPOSITION IN THE FORM OF O/W EMULSION

(71) Applicant: L'OREAL, Paris (FR)

(72) Inventors: Saki Tsuzuki, Kawasaki (JP); Daisuke Misu, Kawasaki (JP)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/535,620

(22) PCT Filed: Dec. 9, 2015

(86) PCT No.: PCT/JP2015/085126
§ 371 (c)(1),
(2) Date: Jun. 13, 2017

(87) PCT Pub. No.: WO2016/098786
PCT Pub. Date: Jun. 23, 2016

(65) Prior Publication Data
US 2017/0326041 A1    Nov. 16, 2017

(30) Foreign Application Priority Data

Dec. 16, 2014 (JP) ................................. 2014-253782

(51) Int. Cl.
| | | |
|---|---|---|
| *A61K 8/06* | (2006.01) | |
| *A61K 8/19* | (2006.01) | |
| *A61K 8/31* | (2006.01) | |
| *A61K 8/34* | (2006.01) | |
| *A61Q 5/06* | (2006.01) | |
| *A61Q 5/08* | (2006.01) | |
| *A61Q 5/10* | (2006.01) | |

(52) U.S. Cl.
CPC ................ *A61K 8/062* (2013.01); *A61K 8/19* (2013.01); *A61K 8/31* (2013.01); *A61K 8/342* (2013.01); *A61K 8/345* (2013.01); *A61Q 5/06* (2013.01); *A61Q 5/08* (2013.01); *A61Q 5/10* (2013.01); *A61K 2800/596* (2013.01)

(58) Field of Classification Search
None
See application file for complete search history.

(56) References Cited

U.S. PATENT DOCUMENTS

| | | | | |
|---|---|---|---|---|
| 6,695,887 | B2 * | 2/2004 | Cottard | .................. A61K 8/342 8/405 |
| 2003/0206955 | A1 * | 11/2003 | Sonneville-Aubrun | ...................... A61K 8/062 424/486 |
| 2011/0232667 | A1 | 9/2011 | Hercouet et al. | |
| 2013/0189206 | A1 | 7/2013 | Goget et al. | |
| 2014/0165298 | A1 | 6/2014 | Neuba et al. | |
| 2014/0165300 | A1 * | 6/2014 | Neuba | ...................... A61K 8/34 8/406 |
| 2016/0151266 | A1 | 6/2016 | Neuba et al. | |

FOREIGN PATENT DOCUMENTS

| | | | |
|---|---|---|---|
| DE | 102012223205 A1 * | 6/2014 | ............... A61K 8/34 |
| DE | 102012223205 A1 | 6/2014 | |
| DE | 102012223206 A1 | 6/2014 | |
| DE | 102013215583 A1 | 2/2015 | |
| FR | 2925317 A1 | 6/2009 | |
| JP | 2002-226342 A | 8/2002 | |
| JP | 2005-255535 A | 9/2005 | |
| JP | 2007-145721 A | 6/2007 | |
| JP | 2008-063301 A | 3/2008 | |
| JP | 2010-150223 A | 7/2010 | |
| JP | 2010-275280 A | 12/2010 | |
| JP | 2012-193171 A | 10/2012 | |
| JP | 2012-240943 A | 12/2012 | |
| JP | 2013-060391 A | 4/2013 | |
| JP | 2013-095835 A | 5/2013 | |
| JP | 2013-189422 A | 9/2013 | |
| WO | 2009/080670 A2 | 7/2009 | |
| WO | 2014/192692 A1 | 4/2014 | |
| WO | 2015/093264 A1 | 6/2015 | |

OTHER PUBLICATIONS

International Search Report and Written Opinion for PCT/JP2015/085126, dated Mar. 15, 2016.
Japanese Office Action for Application No. 2014-253782, dated Aug. 27, 2018 with translation.

* cited by examiner

*Primary Examiner* — Michael P Cohen
(74) *Attorney, Agent, or Firm* — The Marbury Law Group, PLLC

(57) ABSTRACT

The present invention relates to a cosmetic composition in the form of an O/W emulsion, and comprises: (a) at least one fatty alcohol; (b) at least one oil; (c) at least one nonionic surfactant having an HLB value of 15 or more; (d) at least one nonionic surfactant having an HLB value of 5 or less; (e) at least one diol having a straight chain of four or more consecutive carbon atoms; (f) at least one alkaline agent selected from the group consisting of ammonia, ammonium hydroxide, ammonium salts, and mixtures thereof; and (g) water. The composition according to the present invention is easy to handle and can provide keratin fibers such as hair with superior cosmetic effects such as good coloring or bleaching effects as well as a good feeling to the touch of the keratin fibers, while controlling malodor due to an ammonia ingredient in the composition.

17 Claims, No Drawings

COMPOSITION IN THE FORM OF O/W EMULSION

CROSS REFERENCE TO RELATED APPLICATIONS

This is a national stage application of PCT/JP2015/085126, filed internationally on Dec. 9, 2015, which claims priority to Japanese Application No. 2014-253782, filed on Dec. 16, 2014, both of which are incorporated by reference herein in their entireties.

TECHNICAL FIELD

The present invention relates to a composition in the form of an O/W (oil-in-water) emulsion.

BACKGROUND ART

In addition to higher performance of products for bleaching or coloring hair, consumers of such products are more and more sensitive to the usage quality of the products. From the viewpoint of usage quality, the following, for example, can be regarded as major drawbacks: malodor from ammonia which is typically contained as an alkaline agent in conventional hair bleaching or coloring products; difficulty in handling conventional hair bleaching or coloring products which are in the form of a liquid, gel or cream; and the like.

In order to reduce the problems occurring with the pungent odor of ammonia, it has been proposed to replace totally or partially ammonia with another alkaline agent such as alkanolamine (e.g., monoethanolamine and aminomethylpropanol). However, this modification tends to result in a decrease of the bleaching or coloring efficiency. Also, such non-ammonia type alkaline agents are generally concerned about scalp irritation. Therefore, ammonia still maintains a prominent position as an active alkaline ingredient for hair color.

As an alternative hair bleaching or coloring composition based on ammonia as an alkaline agent, JP-A-2002-226342 discloses an emulsion including emulsified particles with a sufficiently small size such as 10 μm or less, wherein the emulsion is believed to inhibit ammonia odor.

JP-A-2002-226342 discloses that it is possible to control emulsion size by optimizing at least one or two factors selected from: the composition of the emulsion, order of blending and/or agitation level. However, generally, it is necessary to use, for example, special emulsification equipment to make an emulsion including emulsified particles of micron size, and they are not industrially economical. Therefore, efficient and economical malodor reducing technology for a composition for keratin fibers such as hair including an ammonia-based alkaline agent has been required.

DISCLOSURE OF INVENTION

An objective of the present invention is to provide a composition in the form of an O/W emulsion, preferably for keratin fibers, more preferably hair, which can control malodor due to ammonia in the composition, can be easily handled, and can provide keratin fibers with good cosmetic effects such as good bleaching or coloring effects as well as a good feeling to the touch of the keratin fibers.

The above objective of the present invention can be achieved by a composition, in the form of an O/W emulsion, comprising:

(a) at least one fatty alcohol;
(b) at least one oil;
(c) at least one nonionic surfactant having an HLB value of 15 or more;
(d) at least one nonionic surfactant having an HLB value of 5 or less;
(e) at least one diol having a straight chain of four or more consecutive carbon atoms;
(f) at least one alkaline agent selected from the group consisting of ammonia, ammonium hydroxide, ammonium salts, and mixtures thereof; and
(g) water.

The (a) fatty alcohol may be selected from straight or branched, saturated or unsaturated $C_{6-30}$ alcohols, preferably straight or branched, saturated $C_{6-30}$ alcohols, and more preferably straight or branched, saturated $C_{12-20}$ alcohols.

The amount of the (a) fatty alcohol may be from 0.5 to 30% by weight, preferably from 1 to 20% by weight, and more preferably from 3 to 15% by weight, relative to the total weight of the composition.

The (b) oil may be selected from hydrocarbon oils, preferably mineral oil.

The amount of the (b) oil may be from 0.5 to 30% by weight, preferably from 1 to 20% by weight, and more preferably from 3 to 15% by weight, relative to the total weight of the composition.

The (c) nonionic surfactant having an HLB value of 15 or more may be selected from oxyethylenated fatty alcohols comprising more than 10 oxyethylene units, preferably more than 15 oxyethylene units, and more preferably more than 20 oxyethylene units.

The amount of the (c) nonionic surfactant having an HLB value of 15 or more may be from 0.1 to 15% by weight, preferably from 0.5 to 10% by weight, and more preferably from 1 to 5% by weight, relative to the total weight of the composition.

The (d) nonionic surfactant having an HLB value of 5 or less may be selected from fatty acid esters of glycerol.

The amount of the (d) nonionic surfactant having an HLB value of 5 or less may be from 0.1 to 15% by weight, preferably from 0.5 to 10% by weight, and more preferably from 1 to 5% by weight, relative to the total weight of the composition.

The (e) diol having a straight chain of four or more consecutive carbon atoms may be selected from the group consisting of butylene glycol, dibutyleneglycol, polybutyleneglycol, and mixtures thereof.

The amount of the (e) diol having a straight chain of four or more consecutive carbon atoms may be from 0.1 to 20% by weight, preferably from 1 to 15% by weight, and more preferably from 3 to 10% by weight, relative to the total weight of the composition.

The amount of the (f) alkaline agent may be from 0.1 to 10% by weight, preferably from 0.5 to 8% by weight, and more preferably from 1 to 5% by weight, relative to the total weight of the composition.

The weight ratio of the (a) fatty alcohol/the (b) oil may be from 5/1 to 1/5, preferably from 3/1 to 1/3, and more preferably from 2/1 to 1/2.

It is preferable that the composition according to the present invention be a cosmetic composition for keratin fibers, preferably for a hair coloring or bleaching product.

The present invention also relates to a process for preparing a composition as described above, comprising the steps of:

(1) mixing (a) at least one fatty alcohol, (b) at least one oil, (c) at least one nonionic surfactant having an HLB value of 15 or more, (d) at least one nonionic surfactant having an HLB value of 5 or less, (e) at least one diol having a straight chain of four or more consecutive carbon atoms, and water;

(2) adding water to the mixture obtained by step (1) to prepare an oil-in-water [O/W] emulsion; and (3) adding (f) at least one inorganic alkaline agent to the O/W emulsion obtained by step (2).

BEST MODE FOR CARRYING OUT THE INVENTION

After diligent research, the inventors have found that it is possible to provide a composition in the form of an O/W emulsion, preferably for keratin fibers, more preferably hair, which can control malodor due to ammonia in the composition, can be easily handled, and can provide keratin fibers with good cosmetic effects such as good bleaching or coloring effects as well as a good feeling to the touch of the keratin fibers.

In other words, it has been surprisingly found by the inventors that a specific composition in the form of an O/W emulsion, including a combination of specific ingredients can significantly reduce or suppress malodor due to ammonia in the composition, and can be easily handled (e.g., easy to mix with another composition to prepare a uniform mixture), while providing keratin fibers with good cosmetic effects such as good bleaching or coloring effects as well as a good feeling to the touch of the keratin fibers. The above combination does not require any special emulsification equipment, and therefore, the present invention is industrially economical.

Thus, the composition according to the present invention is in the form of an O/W emulsion, and comprises:
(a) at least one fatty alcohol;
(b) at least one oil;
(c) at least one nonionic surfactant having an HLB value of 15 or more;
(d) at least one nonionic surfactant having an HLB value of 5 or less;
(e) at least one diol having a straight chain of four or more consecutive carbon atoms;
(f) at least one alkaline agent selected from the group consisting of ammonia, ammonium hydroxide, ammonium salts, and mixtures thereof; and
(g) water.

Hereafter, the composition according to the present invention will be described in a detailed manner.

[Fatty Alcohol]

The composition according to the present invention comprises at least one (a) fatty alcohol, which is different from the oil b). Two or more fatty alcohols may be used.

The term "fatty" here means the inclusion of a relatively large number of carbon atoms. Thus, alcohols which have 4 or more, preferably 6 or more, and more preferably 12 or more carbon atoms are encompassed within the scope of fatty alcohols. The (a) fatty alcohol may be saturated or unsaturated. The (a) fatty alcohol may be linear or branched. The (a) fatty alcohol may be monoalcohol or polyalcohol, and preferably monoalcohol.

The (a) fatty alcohol may have the structure R—OH wherein R is chosen from saturated and unsaturated, linear and branched radicals containing from 4 to 40 carbon atoms, preferably from 6 to 30 carbon atoms, and more preferably from 12 to 20 carbon atoms. In at least one embodiment, R may be chosen from $C_{12}$-$C_{20}$ alkyl and $C_{12}$-$C_{20}$ alkenyl groups. R may be or may not be substituted with at least one hydroxyl group.

As examples of the (a) fatty alcohol, mention may be made of lauryl alcohol, cetyl alcohol, stearyl alcohol, isostearyl alcohol, behenyl alcohol, undecylenyl alcohol, myristyl alcohol, oleyl alcohol, linoleyl alcohol, palmitoleyl alcohol, arachidonyl alcohol, erucyl alcohol, and mixtures thereof.

It is preferable that (a) fatty alcohol be a saturated fatty alcohol.

Thus, the (a) fatty alcohol may be selected from straight or branched, saturated or unsaturated $C_{6-30}$ alcohols, preferably straight or branched, saturated $C_{6-30}$ alcohols, and more preferably straight or branched, saturated $C_{12-20}$ alcohols.

The term "saturated fatty alcohol" here means an alcohol having a long aliphatic saturated carbon chain. It is preferable that the saturated fatty alcohol be selected from any linear or branched, saturated $C_6$-$C_{30}$ fatty alcohols. Among the linear or branched, saturated $C_6$-$C_{30}$ fatty alcohols, linear or branched, saturated $C_{12}$-$C_{20}$ fatty alcohols may preferably be used. Any linear or branched, saturated $C_{16}$-$C_{18}$ fatty alcohols may be more preferably used.

As examples of saturated fatty alcohols, mention may be made of lauryl alcohol, cetyl alcohol, stearyl alcohol, isostearyl alcohol, behenyl alcohol, undecylenyl alcohol, myristyl alcohol, and mixtures thereof. In one embodiment, cetyl alcohol, stearyl alcohol or a mixture thereof (e.g., cetearyl alcohol) as well as behenyl alcohol, can be used as a saturated fatty alcohol.

According to at least one embodiment, the (a) fatty alcohol used in the composition according to the present invention is preferably chosen from cetyl alcohol, stearyl alcohol and cetearyl alcohol. Cetearyl alcohol is more preferable.

Preferably, the (a) fatty alcohols are linear fatty alcohols.

The (a) fatty alcohol may be or may not be oxyalkylenated or glycerolated. Preferably the fatty alcohol is not alkoxylenated nor glycerolated.

According to one embodiment of the present invention, the amount of the (a) fatty alcohol(s) may range from 0.5 to 30% by weight, preferably from 1 to 20% by weight, and more preferably from 3 to 15% by weight, relative to the total weight of the composition according to the present invention.

[Oil]

The composition according to the present invention comprises at least one (b) oil. Two or more oils may be used.

Here, "oil" means a fatty compound or substance which is in the form of a liquid at room temperature (25° C.) under atmospheric pressure (760 mmHg). As the oil(s), those generally used in cosmetics can be used alone or in combination thereof. The oil(s) may be volatile or non-volatile, preferably non-volatile. The oil does not include fatty alcohols The (b) oil may be a non-polar oil such as a hydrocarbon oil, a silicone oil, or the like; a polar oil such as a plant or animal oil and an ester oil or an ether oil; or a mixture thereof.

It is preferable that the (b) oil be selected from the group consisting of oils of plant or animal origin, synthetic oils, silicone oils and hydrocarbon oils.

As examples of plant oils, mention may be made of, for example, linseed oil, *camellia* oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, and mixtures thereof.

As examples of animal oils, mention may be made of, for example, squalene and squalane.

As examples of synthetic oils, mention may be made of alkane oils such as isododecane and isohexadecane, ester oils, ether oils and artificial triglycerides.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the present invention are derived is branched.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of non-sugar $C_4$-$C_{26}$ dihydroxy, trihydroxy, tetrahydroxy or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; and diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters, as well as pentaerythrityl tetraethyl hexanoate.

More particularly, use is made of monoesters and diesters and especially sucrose, glucose or methylglucose monooleates or dioleates, stearates, behenates, oleopalmitates, linoleates, linolenates and oleostearates.

An example that may be mentioned is the product sold under the name Glucate® DO by the company Amerchol, which is a methylglucose dioleate.

As examples of preferable ester oils, mention may be made of, for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof.

As examples of ether oils, mention may be made of, for example, dicaprylylether and diisocetylether.

As examples of artificial triglycerides, mention may be made of, for example, glyceryl trimyristate, glyceryl tripalmitate, glyceryl trilinolenate, glyceryl trilaurate, glyceryl tricaprate, glyceryl tricaprylate, glyceryl tri(caprate/caprylate) and glyceryl tri(caprate/caprylate/linolenate).

As examples of silicone oils, mention may be made of, for example, linear organopolysiloxanes such as dimethylpolysiloxane, methylphenylpolysiloxane, methylhydrogenpolysiloxane, and the like; cyclic organopolysiloxanes such as octamethylcyclotetrasiloxane, decamethylcyclopentasiloxane, dodecamethylcyclohexasiloxane, and the like; and mixtures thereof.

Preferably, the silicone oil is chosen from liquid polydialkylsiloxanes, especially liquid polydimethylsiloxanes (PDMS) and liquid polyorganosiloxanes comprising at least one aryl group.

These silicone oils may also be organomodified. The organomodified silicones that can be used in accordance with the present invention are silicone oils as defined above and comprising in their structure one or more organofunctional groups attached via a hydrocarbon-based group.

Organopolysiloxanes are defined in greater detail in Walter Noll's *Chemistry and Technology of Silicones* (1968), Academic Press. They may be volatile or non-volatile.

Volatile or non-volatile silicone oils, such as volatile or non-volatile polydimethylsiloxanes (PDMS) containing a linear or cyclic silicone chain, that are liquid or pasty at ambient temperature, in particular cyclopolydimethylsiloxanes (cyclomethicones) such as cyclohexasiloxane; polydimethylsiloxanes containing alkyl, alkoxy or phenyl groups that are pendent or at the end of the silicone chain, which groups have from 2 to 24 carbon atoms; phenyl silicones such as phenyl trimethicones, phenyl dimethicones, phenyltrimethylsiloxydiphenylsiloxanes, diphenyl dimethicones, diphenylmethyldiphenyltrisiloxanes, 2-phenylethyltrimethyl siloxysilicates, and polymethylphenylsiloxanes, may be used.

Hydrocarbon oils may be chosen from:

linear or branched, optionally cyclic, $C_6$-$C_{16}$ lower alkanes. Examples that may be mentioned include hexane, undecane, dodecane, tridecane, and isoparaffins, for instance isohexadecane, isododecane and isodecane; and linear or branched hydrocarbons containing more than 16 carbon atoms, such as liquid paraffins, liquid petroleum jelly, polydecenes and hydrogenated polyisobutenes such as Parleam®, and squalane.

As preferable examples of hydrocarbon oils, mention may be made of, for example, linear or branched hydrocarbons such as mineral oils (e.g., liquid paraffin), paraffin, vaseline or petrolatum, naphthalenes, and the like; hydrogenated polyisobutene, isoeicosan, and decene/butene copolymer; and mixtures thereof.

It is preferable that the (b) oil be chosen from hydrocarbon oils which are in the form of a liquid at a room temperature, more preferably mineral oils.

According to one embodiment of the present invention, the amount of the (b) oil(s) may range from 0.5 to 30% by weight, preferably from 1 to 20% by weight, and more preferably from 3 to 15% by weight, relative to the total weight of the composition according to the present invention.

It is preferable that the weight ratio of the (a) fatty alcohol/the (b) oil be from 5/1 to 1/5, preferably from 3/1 to 1/3, and more preferably from 2/1 to 1/2.

[Nonionic Surfactant Having HLB Value of 15 or More]

The composition according to the present invention comprises at least one (c) nonionic surfactant having an HLB value of 15 or more. Two or more nonionic surfactants each of which has an HLB value of 15 or more may be used.

The HLB is the ratio between the hydrophilic part and the lipophilic part in the molecule. This term HLB is well known to those skilled in the art and is described in "The HLB system. A time-saving guide to emulsifier selection" (published by ICI Americas Inc., 1984).

The term HLB ("hydrophilic-lipophilic balance") is well known to those skilled in the art, and denotes the hydrophilic-lipophilic balance of a surfactant.

The HLB or hydrophilic-lipophilic balance of the surfactant(s) used according to the present invention is the HLB according to Griffin, defined in the publication *J Soc. Cosm. Chem.*, 1954 (Vol 5), pages 249-256 or the HLB determined experimentally and as described in the publication from the authors F. Puisieux and M. Seiller, entitled "Galenica 5: Les systèmes dispersés [Dispersed systems]—Volume I—Agents de surface et émulsions [Surface agents and emulsions]—Chapter IV—Notions de HLB et de HLB critique [Notions of HLB and of critical HLB], pages 153-194—paragraph 1.1.2. Détermination de HLB par voie expérimentale [Experimental determination of HLB], pages 164-180.

It may be useful to use a combination of a (c) nonionic surfactant having an HLB value of 15.0 or more, and of a (c) nonionic surfactant having an HLB value of 16.0 or more, preferably 17.0 or more, and more preferably 18.0 or more.

Nonionic surfactants are compounds well known in themselves (see, e.g., in this regard, "Handbook of Surfactants" by M. R. Porter, Blackie & Son publishers (Glasgow and London), 1991, pp. 116-178). Thus, they can, for example, be chosen from alcohols, alpha-diols, alkylphenols, and esters of fatty acids, which are polyethoxylated, polypropoxylated or polyglycerolated and have at least one fatty chain comprising, for example, from 8 to 18 carbon atoms, it being possible for the number of ethylene oxide or propylene oxide groups to range from 20 to 50, and for the number of glycerol groups to range from 20 to 40. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 20 to 40 ethylene oxide groups; polyglycerolated fatty amides comprising, for example, from 20 to 40 glycerol groups; ethoxylated fatty acid esters of sorbitan comprising from 20 to 40 ethylene oxide groups; ethoxylated oils of plant origin; fatty acid esters of sucrose; fatty acid esters of polyethylene glycol; fatty acid esters of glycerol; ($C_6$-$C_{24}$) alkylpolyglycosides; N—($C_6$-$C_{24}$) alkylglucamine derivatives, amine oxides such as ($C_{10}$-$C_{14}$) alkylamine oxides or N—($C_{10}$-$C_{14}$) acylaminopropylmorpholine oxides; and mixtures thereof.

The nonionic surfactants may preferably be chosen from oxyalkylenated nonionic surfactants, e.g., monooxyalkylenated or polyoxyalkylenated nonionic surfactants, and glycerolated nonionic surfactants, e.g., monoglycerolated or polyglycerolated nonionic surfactants. The oxyalkylene units are more particularly oxyethylene or oxypropylene units, or a combination thereof, preferably oxyethylene units.

Examples of oxyalkylenated nonionic surfactants that may be mentioned include: oxyalkylenated ($C_8$-$C_{24}$) alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyalkylenated esters of saturated or unsaturated, linear or branched, $C_8$-$C_{30}$ acids and of sorbitol, saturated or unsaturated, oxyalkylenated plant oils, and condensates of ethylene oxide and/or of propylene oxide, inter alia, alone or as mixtures.

The surfactants may contain a number of moles of ethylene oxide and/or of propylene oxide of between 20 and 100, preferably between 20 and 70, and more preferably from 20 to 40. Advantageously, the nonionic surfactants do not comprise any oxypropylene units.

In accordance with one preferred embodiment of the present invention, the oxyalkylenated nonionic surfactants may be chosen from oxyethylenated fatty alcohols (polyethylene glycol ether of fatty alcohol) and oxyethylenated fatty esters (polyethylene glycol ester of fatty acids), preferably oxyethylenated fatty alcohol.

It is preferable that the (c) nonionic surfactant having an HLB value of 15 or more be selected from oxyethylenated fatty alcohols comprising more than 10 oxyethylene units, preferably 15 oxyethylene units, and more preferably 20 oxyethylene units.

Examples of oxyethylenated fatty alcohols that may be mentioned include the adducts of ethylene oxide with lauryl alcohol, especially those containing from 15 to 50 oxyethylene groups and more particularly those containing from 20 to 40 oxyethylene groups (Laureth-20 to Laureth-40, such as Laureth-20, Laureth-23, Laureth-25, and Laureth-30, as the CTFA names); the adducts of ethylene oxide with behenyl alcohol, especially those containing from 15 to 50 oxyethylene groups and more particularly those containing from 20 to 40 oxyethylene groups (Beheneth-20 to Beheneth-40, as the CTFA names); the adducts of ethylene oxide with cetearyl alcohol (mixture of cetyl alcohol and stearyl alcohol), especially those containing from 15 to 50 oxyethylene groups and more particularly those containing from 20 to 40 oxyethylene groups (Ceteareth-20 to Ceteareth-40, such as Ceteareth-25 and Ceteareth-33, as the CTFA names); the adducts of ethylene oxide with cetyl alcohol, especially those containing from 15 to 50 oxyethylene groups and more particularly those containing from 25 to 40 oxyethylene groups (e.g., Ceteth-25 to Ceteth-40, such as Ceteth-30, as the CTFA names); the adducts of ethylene oxide with stearyl alcohol, especially those containing from 15 to 50 oxyethylene groups and more particularly those containing from 20 to 40 oxyethylene groups (e.g., Steareth-20 to Steareth-40, such as Steareth-20, Steareth-25 and Steareth-30, as the CTFA names); the adducts of ethylene oxide with isostearyl alcohol, especially those containing from 15 to 50 oxyethylene groups and more particularly those containing from 25 to 50 oxyethylene groups (Isosteareth-25 to Isosteareth-50, as the CTFA names); the adducts of ethylene oxide with oleyl alcohol, especially those containing from 15 to 50 oxyethylene groups and more particularly those containing from 25 to 40 oxyethylene groups (Oleth-25 to Oleth-40, such as Oleth-30, as the CTFA names); and mixtures thereof.

Examples of oxyethylenated fatty esters that may be mentioned include the adducts of ethylene oxide with esters of lauric acid, palmitic acid, stearic acid or behenic acid, and mixtures thereof, especially those containing from 32 to 150 oxyethylene groups, such as PEG-32 to PEG-150 dilaurate (as the CTFA names: PEG-32 dilaurate to PEG-150 dilaurate); PEG-30 to PEG-150 stearate (as the CTFA names: PEG-30 stearate to PEG-150 stearate); PEG-32 to PEG-150 distearate (as the CTFA names: PEG-32 distearate to PEG-150 distearate); PEG-32 to PEG-150 dioleate (as the CTFA names: PEG-32 dioleate to PEG-150 dioleate); and mixtures thereof.

Mixtures of these oxyethylenated derivatives of fatty alcohols and of fatty esters may also be used.

According to one preferred embodiment of the present invention, the nonionic surfactant may be oxyethylenated fatty alcohol.

As examples of monoglycerolated or polyglycerolated nonionic surfactants, monoglycerolated or polyglycerolated $C_8$-$C_{40}$ alcohols, and monoglycerolated or polyglycerolated $C_8$-$C_{40}$ fatty acid esters, are preferably used.

The monoglycerolated or polyglycerolated $C_8$-$C_{40}$ alcohols may correspond to the following formula:

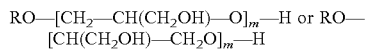

in which R represents a linear or branched $C_8$-$C_{40}$ and preferably $C_8$-$C_{30}$ alkyl or alkenyl radical, and m represents a number ranging from 10 to 50 and preferably from 20 to 40.

The monoglycerolated or polyglycerolated $C_8$-$C_{40}$ fatty acid esters may correspond to the following formula:

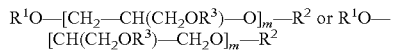

in which each of $R^1$, $R^2$ and $R^3$ independently represents a hydrogen atom, or a linear or branched $C_8$-$C_{40}$ and preferably $C_8$-$C_{30}$ alkyl-CO— or alkenyl-CO-radical, with the proviso that at least one of $R^1$, $R^2$ and $R^3$ is not a hydrogen atom, and m represents a number ranging from 10 to 50 and preferably from 20 to 40.

According to one embodiment of the present invention, the amount of the (c) nonionic surfactant(s) having an HLB value of 15 or more may range from 0.1 to 15% by weight, preferably from 0.5 to 10% by weight, and more preferably from 1 to 5% by weight, relative to the total weight of the composition according to the present invention.

[Nonionic Surfactant Having HLB Value of 5 or Less]

The composition according to the present invention comprises at least one (d) nonionic surfactant having an HLB value of 5 or less. Two or more nonionic surfactants each of which has an HLB value of 5 or less may be used.

It may be useful to use a combination of the (d) nonionic surfactant having an HLB value of 5.0 or less, and of the (d) nonionic surfactant having an HLB value of 5.0 or less, preferably 4.5 or less, and more preferably 4.0 or less.

The nonionic surfactants may preferably be chosen from oxyalkylenated nonionic surfactants, e.g., monooxyalkylenated or polyoxyalkylenated nonionic surfactants, and glycerolated nonionic surfactants, e.g., monoglycerolated or polyglycerolated nonionic surfactants. The oxyalkylene units are more particularly oxyethylene or oxypropylene units, or a combination thereof, preferably oxyethylene units.

Examples of oxyalkylenated nonionic surfactants that may be mentioned include: oxyalkylenated ($C_8$-$C_{24}$) alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyalkylenated esters of saturated or unsaturated, linear or branched, $C_8$-$C_{30}$ acids and of sorbitol, saturated or unsaturated, oxyalkylenated plant oils, and condensates of ethylene oxide and/or of propylene oxide, inter alia, alone or as mixtures.

The surfactants may contain a number of moles of ethylene oxide and/or of propylene oxide of between 1 and less than 15, preferably between 2 and 10, and more preferably from 2 to 8. Advantageously, the nonionic surfactants do not comprise any oxypropylene units.

In accordance with one preferred embodiment of the present invention, the oxyalkylenated nonionic surfactants may be chosen from oxyethylenated fatty alcohols and oxyethylenated fatty esters, preferably oxyethylenated fatty alcohol.

Examples of oxyethylenated fatty alcohols that may be mentioned include the adducts of ethylene oxide with the adducts of ethylene oxide with stearyl alcohol, especially those containing from 1 to 3 oxyethylene groups and more particularly those containing 2 oxyethylene groups (e.g., Steareth-2, as the CTFA name); the adducts of ethylene oxide with cetyl alcohol, especially those containing from 1 to 3 oxyethylene groups and more particularly those containing 2 oxyethylene groups (e.g., Ceteth-2, as the CTFA name); the adducts of ethylene oxide with isostearyl alcohol, especially those containing from 1 to 3 oxyethylene groups and more particularly those containing 2 oxyethylene groups (Isosteareth-2, as the CTFA name); the adducts of ethylene oxide with oleyl alcohol, especially those containing from 1 to 3 oxyethylene groups and more particularly those containing 2 oxyethylene groups (Oleth-2, as the CTFA name); and mixtures thereof.

Examples of oxyethylenated fatty esters that may be mentioned include the adducts of ethylene oxide with esters of lauric acid, palmitic acid, stearic acid or behenic acid, and mixtures thereof, especially those containing from 2 to 4 oxyethylene groups, such as PEG-2 to PEG-4 dilaurate (as the CTFA names: PEG-2 dilaurate to PEG-4 dilaurate); PEG-2 stearate (as the CTFA name: PEG-2 stearate); PEG-2 to PEG-6 distearate (as the CTFA names: PEG-2 distearate to PEG-6 distearate); PEG-2 to PEG-6 dioleate (as the CTFA names: PEG-2 dioleate to PEG-6 dioleate); and mixtures thereof.

Mixtures of these oxyethylenated derivatives of fatty alcohols and of fatty esters may also be used.

According to one preferred embodiment of the present invention, the nonionic surfactant may be ethoxylated fatty alcohol.

As examples of monoglycerolated or polyglycerolated nonionic surfactants, monoglycerolated or polyglycerolated $C_8$-$C_{40}$ alcohols, and monoglycerolated or polyglycerolated $C_8$-$C_{40}$ fatty acid esters, are preferably used.

The monoglycerolated or polyglycerolated $C_8$-$C_{40}$ alcohols may correspond to the following formula:

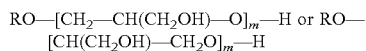

in which R represents a linear or branched $C_8$-$C_{40}$ and preferably $C_8$-$C_{30}$ alkyl or alkenyl radical, and m represents a number ranging from 1 to less than 10 and preferably from 1 to 6.

As examples of compounds that are suitable in the context of the present invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

Among the monoglycerolated or polyglycerolated alcohols, it is more particularly preferred to use a $C_8/C_{10}$ alcohol containing 1 mol of glycerol, a $C_{10}/C_{12}$ alcohol containing 1 mol of glycerol and a $C_{12}$ alcohol containing 1.5 mol of glycerol.

The monoglycerolated or polyglycerolated $C_8$-$C_{40}$ fatty acid esters may correspond to the following formula:

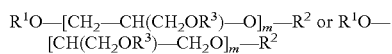

in which each of $R^1$, $R^2$ and $R^3$ independently represents a hydrogen atom, or a linear or branched $C_8$-$C_{40}$ and preferably $C_8$-$C_{30}$ alkyl-CO— or alkenyl-CO-radical, with the proviso that at least one of $R^1$, $R^2$ and $R^3$ is not a hydrogen atom, and m represents a number ranging from 1 to less than 10, and preferably from 1 to 3.

As examples of compounds that are suitable in the context of the present invention, mention may be made of polyglyceryl monolaurate comprising 4 to 6 glycerol units, polyglyceryl mono(iso)stearate comprising 4 to 6 glycerol units, polyglyceryl monooleate comprising 4 to 6 glycerol units, and polyglyceryl dioleate comprising 4 to 6 glycerol units.

The monoglycerolated or polyglycerolated $C_8$-$C_{40}$ fatty acid esters may be esters of glycerin(s) and $C_8$-$C_{40}$ fatty acid, preferably glyceryl stearate (mono-, di- and/or tri-glyceryl stearate) (CTFA name: glyceryl stearate) or glyceryl ricinoleate, and mixtures thereof.

It is preferable that the (d) nonionic surfactant having an HLB value of 5 or less be selected from fatty acid esters of glycerol, more preferably monoglyceryl fatty acids such as monoglyceryl stearate.

According to one embodiment of the present invention, the amount of the (d) nonionic surfactant(s) having an HLB value of 5 or less may range from 0.1 to 15% by weight, preferably from 0.5 to 10% by weight, and more preferably from 1 to 5% by weight, relative to the total weight of the composition according to the present invention.

It may be preferable that the total amount of the (c) nonionic surfactant(s) having an HLB value of 15 or more and the (d) nonionic surfactant having an HLB value of 5 or less be from 1 to 10% by weight, preferably from 2 to 8% by weight, and more preferably from 4 to 7% by weight, relative to the total weight of the composition according to the present invention.

It may be preferable that the weight ratio of the (a) fatty alcohol/(the total amount of the (c) nonionic surfactant(s) having an HLB value of 15 or more and the (d) nonionic surfactant having an HLB value of 5 or less) be from 1 to 5, preferably from 1 to 3, and more preferably from 1 to 2.

[Diol]

The composition according to the present invention comprises at least one (e) diol, different from the oil (b), having a straight chain of four or more consecutive carbon atoms. Two or more (e) diols having a straight chain of four or more consecutive carbon atoms may be used.

The term "diol" here means a compound which has two alcohol functions. In other words, diol is an alcohol having two hydroxyl groups. The (e) diol having a straight chain of four or more consecutive carbon atoms may be a $C_{4-36}$ diol, preferably $C_{4-21}$ diol, and more preferably $C_{4-12}$ diol, comprising 2 hydroxy groups.

The straight chain of four or more consecutive carbon atoms in the (e) diol includes 4 or more carbon atoms which form a straight carbon chain. The number of carbon atoms which form the straight carbon chain is not limited. However, it is preferable that the number of atoms which forms the straight carbon chain be 8 or less, more preferably 6 or less and even more preferably 4. In other words, it is preferable that the (e) diol having a straight chain of four or more consecutive carbon atoms do not have any hydrophobic group such as alkyl or alkenyl groups with more than 8 carbon atoms.

It is preferable that the (e) diol have a straight carbon chain formed by —C—C—C—C—, —C=C—C—C—, —C—C=C—C—, —C≡C—C—C—, —C—C≡C—C—, —C≡C—C=C—, —C=C—C=C— or —C≡C—C≡C— moiety, in the molecule thereof, wherein the carbon atoms which are capable of bonding other atoms may be bonded to hydrogen or halogen atoms, preferably hydrogen atoms. Thus, the (e) diol having a straight chain of four or more consecutive carbon atoms may be saturated or unsaturated, preferably saturated.

The (e) diol having a straight chain of four or more consecutive carbon atoms may have a linear, branched or cyclic molecular structure, as long as the carbon chain of four or more consecutive carbon atoms is straight.

It is preferable that the (e) diol having a straight chain of four or more consecutive carbon atoms be selected from the group consisting of butylene glycol, dibutyleneglycol, polybutyleneglycol, pentyleneglycol, dipentyleneglycol, hexyleneglycol, dihexyleneglycol and mixtures thereof. It is more preferable that the (e) diol having a straight chain of four or more consecutive carbon atoms be selected from the group consisting of butylene glycol, dibutyleneglycol, polybutyleneglycol, and mixtures thereof. Butylene glycol is most preferable.

According to one embodiment of the present invention, the amount of the (e) diol having a straight chain of four or more consecutive carbon atoms may range from 0.1 to 20% by weight, preferably from 1 to 15% by weight, and more preferably from 3 to 10% by weight, relative to the total weight of the composition according to the present invention.

[Alkaline Agent]

The composition according to the present invention comprises at least one (f) alkaline agent selected from the group consisting of ammonia, ammonium hydroxide, ammonium salts, and mixtures thereof. Two or more (f) alkaline agents may be used.

The (f) alkaline agent is preferably an inorganic alkaline agent.

The ammonia does not have to be in the form of gas. According to the present invention, an aqueous solution of ammonia may be used as the (f) alkaline agent. It is clear for a person skilled in the art that an aqueous solution of ammonia may be represented as ammonium hydroxide.

As ammonium salts, mention may be made of inorganic ammonium salts such as ammonium carbonate, ammonium bicarbonate, ammonium chloride, ammonium nitrate, ammonium sulfate, ammonium phosphate; organic ammonium salts such as ammonium formate, ammonium acetate, and tetramethylammonium hydroxide; and mixtures thereof.

As the (f) alkaline agent, ammonia in the form of an aqueous solution (ammonium hydroxide) and inorganic ammonium salts such as ammonium bicarbonate are preferable.

The amount of the (f) alkaline agent(s) may range from 0.1 to 10% by weight, preferably from 0.5 to 8% by weight, more preferably from 1 to 5% by weight, relative to the total weight of the composition according to the present invention.

[Water]

The composition according to the present invention comprises (g) water.

The amount of (g) water is not limited, and may be from 30 to 80% by weight, preferably from 40 to 70% by weight, and more preferably from 50 to 60% by weight, relative to the total weight of the composition according to the present invention.

[Additional Ingredients]

(Additional Surfactant)

The composition according to the present invention may comprise at least one (h) additional surfactant other than the above ingredient (c) or (d). Two or more (h) additional surfactants may be used in combination. Thus, a single type of (h) additional surfactant or a combination of different types of (h) additional surfactants may be used.

The (h) additional surfactant used in the present invention may be selected from the group consisting of (h1) anionic surfactants, (h2) amphoteric surfactants, (h3) cationic surfactants, and (h4) nonionic surfactants having an HLB value of more than 5 and less than 15.

It is preferable that the (h) additional surfactants be selected from (h1) anionic surfactants.

(h1) Anionic Surfactants

According to the present invention, the type of anionic surfactant is not limited. It is preferable that the anionic surfactant be selected from the group consisting of ($C_6$-$C_{30}$) alkyl sulfates, ($C_6$-$C_{30}$) alkyl ether sulfates, ($C_6$-$C_{30}$) alkylamido ether sulfates, alkylaryl polyether sulfates, monoglyceride sulfates; ($C_6$-$C_{30}$) alkylsulfonates, ($C_6$-$C_{30}$) alkylamide sulfonates, ($C_6$-$C_{30}$) alkylaryl sulfonates, α-olefin sulfonates, paraffin sulfonates; ($C_6$-$C_{30}$) alkyl phosphates; ($C_6$-$C_{30}$) alkyl sulfosuccinates, ($C_6$-$C_{30}$) alkyl ether sulfosuccinates, ($C_6$-$C_{30}$) alkylamide sulfosuccinates; ($C_6$-$C_{30}$) alkyl sulfoacetates; ($C_6$-$C_{24}$) acyl sarcosinates; ($C_6$-$C_{24}$) acyl glutamates; ($C_6$-$C_{30}$) alkylpolyglycoside carboxylic ethers; ($C_6$-$C_{30}$) alkylpolyglycoside sulfosuccinates; ($C_6$-$C_{30}$) alkyl sulfosuccinamates; ($C_6$-$C_{24}$) acyl isethionates; N—($C_6$-$C_{24}$) acyl taurates; $C_6$-$C_{30}$ fatty acid salts; coconut oil acid salts or hydrogenated coconut oil acid salts; ($C_8$-$C_{20}$) acyl lactylates; ($C_6$-$C_{30}$) alkyl-D-galactoside uronic acid salts; polyoxyalkylenated ($C_6$-$C_{30}$) alkyl ether carboxylic acid salts; polyoxyalkylenated ($C_6$-$C_{30}$) alkylaryl ether carboxylic acid salts; polyoxyalkylenated ($C_6$-$C_{30}$) alkylamido ether carboxylic acid salts; and polyoxyalkylenated ($C_6$-$C_{30}$) alkyl ether phosphates.

It is more preferable that the anionic surfactant be selected from salts of $C_6$-$C_{30}$ fatty acids, ($C_6$-$C_{30}$) alkyl phosphate and polyoxyalkylenated ($C_6$-$C_{30}$) alkyl ether phosphates.

In at least one embodiment, the anionic surfactants are in the form of salts such as salts of alkali metals, for instance sodium; salts of alkaline-earth metals, for instance magnesium; ammonium salts; amine salts; and amino alcohol salts. Depending on the conditions, they may also be in acid form.

It should be noted that the alkyl or acyl radicals of these various compounds can contain from 12 to 20 carbon atoms. Moreover, for instance, the aryl radical can be chosen from a phenyl or benzyl group.

Furthermore, the polyoxyalkylenated anionic surfactants can, for example, comprise from 2 to 50 alkylene oxide, for instance ethylene oxide, groups.

In accordance with at least one embodiment of the present disclosure, the anionic surfactant can be chosen from stearic acid, dicetyl phosphate and ceteth-10 phosphate.

(h2) Amphoteric Surfactants

According to the present invention, the type of amphoteric surfactant is not limited. The amphoteric or zwitterionic surfactants can be, for example (non-limiting list), amine derivatives such as aliphatic secondary or tertiary amines, and optionally quaternized amine derivatives, in which the aliphatic radical is a linear or branched chain comprising 8 to 22 carbon atoms and containing at least one water-solubilizing anionic group (for example, carboxylate, sulphonate, sulphate, phosphate or phosphonate).

The amphoteric surfactant may preferably be selected from the group consisting of betaines and amidoaminecarboxylated derivatives.

The betaine-type amphoteric surfactant is preferably selected from the group consisting of alkylbetaines, alkylamidoalkylbetaines, sulfobetaines, phosphobetaines, and alkylamidoalkylsulfobetaines, in particular, ($C_8$-$C_{24}$) alkylbetaines, ($C_8$-$C_{24}$) alkylamido ($C_1$-$C_8$) alkylbetaines, sulphobetaines, and ($C_8$-$C_{24}$) alkylamido ($C_1$-$C_8$) alkylsulphobetaines. In one embodiment, the amphoteric surfactants of betaine type are chosen from ($C_8$-$C_{24}$) alkylbetaines, ($C_8$-$C_{24}$) alkylamido($C_1$-$C_8$) alkylsulphobetaines, sulphobetaines, and phosphobetaines.

Non-limiting examples that may be mentioned include the compounds classified in the CTFA dictionary, 9th edition, 2002, under the names cocobetaine, laurylbetaine, cetylbetaine, coco/oleamidopropylbetaine, cocamidopropylbetaine, palmitamidopropylbetaine, stearamidopropylbetaine, cocamidoethylbetaine, cocamidopropylhydroxysultaine, oleamidopropylhydroxysultaine, cocohydroxysultaine, laurylhydroxysultaine, and cocosultaine, alone or as mixtures.

The betaine-type amphoteric surfactant is preferably an alkylbetaine and an alkylamidoalkylbetaine, in particular cocobetaine and cocamidopropylbetaine.

Among the amidoaminecarboxylated derivatives, mention may be made of the products sold under the name Miranol, as described in U.S. Pat. Nos. 2,528,378 and 2,781,354 and classified in the CTFA dictionary, 3rd edition, 1982 (the disclosures of which are incorporated herein by reference), under the names Amphocarboxyglycinates and Amphocarboxypropionates, with the respective structures:

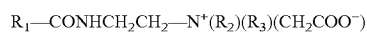

$R_1$—CONHCH$_2$CH$_2$—N$^+$($R_2$)($R_3$)(CH$_2$COO$^-$)

in which:

$R_1$ denotes an alkyl radical of an acid $R_1$—COOH present in hydrolysed coconut oil, a heptyl, nonyl or undecyl radical, $R_2$ denotes a beta-hydroxyethyl group, and $R_3$ denotes a carboxymethyl group; and

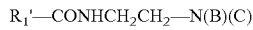

in which:

B represents —$CH_2CH_2OX'$,

C represents —$(CH_2)_z$—Y', with z=1 or 2,

X' denotes a —$CH_2CH_2$—COOH group, —$CH_2$—COOZ', —$CH_2CH_2$—COOH, —$CH_2CH_2$—COOZ' or a hydrogen atom, Y' denotes —COOH, —COOZ', —$CH_2$—CHOH—$SO_3Z'$ or a —$CH_2$—CHOH—$SO_3H$ radical, Z' represents an ion of an alkaline or alkaline earth metal such as sodium, an ammonium ion or an ion issued from an organic amine, and $R_1'$ denotes an alkyl radical of an acid $R_1'$—COOH present in coconut oil or in hydrolysed linseed oil, an alkyl radical, such as a $C_7$, $C_9$, $C_{11}$ or $C_{13}$ alkyl radical, a $C_{17}$ alkyl radical and its iso form, or an unsaturated $C_{17}$ radical.

It is preferable that the amphoteric surfactant be selected from ($C_8$-$C_{24}$) alkyl amphomonoacetates, ($C_8$-$C_{24}$) alkyl amphodiacetates, ($C_8$-$C_{24}$) alkyl amphomonopropionates, and ($C_8$-$C_{24}$) alkyl amphodipropionates.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphopropionate, Disodium Caprylamphodipropionate, Disodium Caprylamphodipropionate, Lauroamphodipropionic acid and Cocoamphodipropionic acid.

By way of example, mention may be made of the cocoamphodiacetate sold under the trade name Miranol® C2M concentrate by the company Rhodia Chimie.

(h3) Cationic Surfactants

According to the present invention, the type of cationic surfactant is not limited. The cationic surfactant may be selected from the group consisting of optionally polyoxyalkylenated, primary, secondary or tertiary fatty amine salts, quaternary ammonium salts, and mixtures thereof.

Non-limiting examples of the quaternary ammonium salt that may be mentioned include salts, for example chloride and methyl sulfate, of diacyloxyethyl-dimethylammonium, of diacyloxyethyl-hydroxyethyl-methylammonium, of monoacyloxyethyl-dihydroxyethyl-methylammonium, of triacyloxyethyl-methylammonium, of monoacyloxyethyl-hydroxyethyl-dimethylammonium, and mixtures thereof. In one embodiment, the acyl radicals may comprise from 14 to 18 carbon atoms, and may be derived, for example, from a plant oil, for instance palm oil and sunflower oil. When the compound comprises several acyl radicals, these radicals may be identical or different.

These products may be obtained, for example, by direct esterification of optionally oxyalkylenated triethanolamine, triisopropanolamine, alkyldiethanolamine or alkyldiisopropanolamine onto fatty acids or onto mixtures of fatty acids of plant or animal origin, or by transesterification of the methyl esters thereof. This esterification may be followed by a quaternization using an alkylating agent chosen from alkyl halides, for example methyl and ethyl halides; dialkyl sulfates, for example dimethyl and diethyl sulfates; methyl methanesulfonate; methyl para-toluenesulfonate; glycol chlorohydrin; and glycerol chlorohydrin.

Such compounds are sold, for example, under the names Dehyquart® by the company Cognis, Stepanquat® by the company Stepan, Noxamium® by the company Ceca, and "Rewoquat® WE 18" by the company Rewo-Goldschmidt.

Other non-limiting examples of ammonium salts that may be used in the compositions according to the present invention include the ammonium salts comprising at least one ester function described in U.S. Pat. Nos. 4,874,554 and 4,137,180.

Among the quaternary ammonium salts mentioned above that may be used in compositions according to the present invention include, but are not limited to, for example tetraalkylammonium chlorides, for instance dialkyldimethylammonium and alkyltrimethylammonium chlorides in which the alkyl radical comprises from about 12 to 22 carbon atoms, such as behenyltrimethylammonium, distearyldimethylammonium, cetyltrimethylammonium and benzyldimethylstearylammonium chloride; palmitylamidopropyltrimethylammonium chloride; and stearamidopropyldimethyl(myristyl acetate)ammonium chloride, sold under the name "Ceraphyl® 70" by the company Van Dyk.

According to one embodiment, the cationic surfactant that may be used in the compositions of the present invention is chosen from quaternary ammonium salts, for example from behenyltrimethylammonium chloride, cetyltrimethylammonium chloride, Quaternium-83, Quaternium-87, Quaternium-22, behenylamidopropyl-2,3-dihydroxypropyldimethylammonium chloride, palmitylamidopropyltrimethylammonium chloride, and stearamidopropyldimethylamine.

(h4) Nonionic Surfactants

According to the present invention, the type of nonionic surfactant having an HLB value of more than 5 and less than 15 is not limited.

According to one embodiment of the present invention, the amount of the (h) additional surfactant(s) may range from 0.01 to 10% by weight, preferably from 0.1 to 5% by weight, and more preferably from 0.3 to 1% by weight, relative to the total weight of the composition according to the present invention.

It may be preferable that the total amount of the surfactants in the composition according to the present invention range from 0.5 to 30% by weight, preferably from 1 to 20% by weight, and more preferably from 5 to 10% by weight, relative to the total weight of the composition according to the present invention.

It may be preferable that the average of the HLB value of the total surfactants in the composition according to the present invention range from 6 to 16, preferably from 7 to 15, and more preferably from 8 to 14.

The average HLB is determined by the weight average of the HLB values of all the surfactants, if two or more surfactants are used. For example, the HLB value of a mixture of 3.0% by weight of Steareth-20 (HLB:15.5) and 2.5% by weight of Ceteth-10 (HLB:12.9) is calculated as follows: {15.5*3.0+12.9*2.5}/{3.0+2.5}=14.3.

(Polyol)

The composition according to the present invention may comprise at least one (i) polyol other than the above ingredient (e). Two or more (i) polyols may be used.

The term "polyol" here means a compound which has a plurality of alcohol functions. In other words, polyol is an alcohol having two or more hydroxyl groups. The polyol may be a $C_2$-$C_{12}$ polyol, preferably a $C_{2-9}$ polyol, comprising at least 2 hydroxy groups, and preferably 2 to 5 hydroxy groups. In the scope of this invention, the polyols are without hydrophobic groups such as alkyl or alkenyl groups with more than 8 atoms of carbon.

The (i) polyol may be a natural or synthetic polyol. The (i) polyol may have a linear, branched or cyclic molecular structure.

Polyols which can be used in the present invention include, in particular, diols or glycols such as ethyleneglycol, and propyleneglycol; polyglycols such as diethyleneglycol, dipropylene glycol, polyethyleneglycol, and polypropyleneglycol; triols such as glycerol; and a mixture thereof.

It is preferable that the (i) polyol be other than ethyleneglycol or propyleneglycol.

It may be preferable that the (i) polyol be selected from the group consisting of a sugar, a sugar alcohol and a triol.

The term "sugar" here means an oxygen-bearing hydrocarbon-based compound containing several alcohol functions, with or without aldehyde or ketone functions, and which contains at least 4 carbon atoms. These sugars may be monosaccharides, oligosaccharides or polysaccharides.

Examples of suitable sugars that may be mentioned include sucrose (or saccharose), glucose, galactose, ribose, fructose, maltose, mannose, arabinose, xylose, trehalose, and lactose, and derivatives thereof, especially alkyl derivatives, such as methyl derivatives, for instance methylglucose.

The term "sugar alcohol" here means a compound obtained by the reduction of the possible ketone or aldehyde group of a sugar to an alcohol group. Thus, a sugar alcohol has several alcohol functions.

Examples of suitable sugar alcohols that may be mentioned include sorbitol, xylitol, erythritol, pentaerythritol, arabitol, and derivatives thereof.

The term "triol" here means an alcohol which has three hydroxyl groups. An example of a triol is glycerol or glycerin.

The (i) polyol may be selected from glycerins and derivatives thereof, and glycols and derivatives thereof. The polyol may be selected from the group consisting of glycerin, diglycerin, and polyglycerin.

According to one embodiment of the present invention, the amount of the (i) polyol(s) may range from 0.5 to 20% by weight, preferably from 1 to 15% by weight, and more preferably from 3 to 10% by weight, relative to the total weight of the composition according to the present invention.

(Cosmetic Active Ingredient)

The composition according to the present invention may comprise at least one (j) cosmetic active ingredient. Two or more (j) cosmetic active ingredients may be used.

According to the present invention, the type of (j) cosmetic active ingredient is not limited, as long as the (j) cosmetic active ingredient can provide any cosmetic effects such as coloring, bleaching, straightening, perming, conditioning and the like to a keratin substance in particular keratin fibers such as hair.

In one embodiment, the (j) cosmetic active ingredient may be a cationic polymer.

(Cationic Polymer)

It should be noted that, for the purposes of the present invention, the term "cationic polymer" denotes any polymer containing cationic groups and/or groups that may be ionized into cationic groups.

Such polymers may be chosen from those already known per se as improving the cosmetic properties of the hair, i.e., especially those described in patent application EP-A-337 354 and in French patents FR-2 270 846, 2 383 660, 2 598 611, 2 470 596 and 2 519 863.

The cationic polymers that are preferred are chosen from those containing units including primary, secondary, tertiary and/or quaternary amine groups, which may either form part of the main polymer chain or may be borne by a side substituent directly attached thereto.

The cationic polymers used generally have a number-average molecular mass of between approximately 500 and approximately $5*10^6$ and preferably between approximately $10^3$ and approximately $3*10^6$.

Among the cationic polymers that may be mentioned more particularly are polymers of the polyamine, polyamino amide and polyquaternary ammonium type.

These are known products. They are described in particular in French patents 2 505 348 and 2 542 997. Among the said polymers, mention may be made of the following.

(1) Homopolymers or copolymers derived from acrylic or methacrylic esters or amides;
(2) Cationic polysaccharides, such as Cationic cellulose derivatives, and Cationic guar gums;
(3) Polymers consisting of piperazinyl units and of divalent alkylene or hydroxyalkylene radicals containing straight or branched chains, optionally interrupted by oxygen, sulfur or nitrogen atoms or by aromatic or heterocyclic rings, and also the oxidation and/or quaternization products of these polymers;
(4) Water-soluble polyamino amides prepared in particular by polycondensation of an acidic compound with a polyamine;
(5) The polyamino amide derivatives resulting from the condensation of polyalkylene polyamines with polycarboxylic acids followed by alkylation with difunctional agents;
(6) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms;
(7) Cyclopolymers of alkyldiallylamine or of dialkyldiallylammonium;
(8) The quaternary diammonium polymer;
(9) Quaternary polymers of vinylpyrrolidone and of vinylimidazole;
(10) Polyamines such as Polyquart H sold by Henkel, which is given under the reference name "Polyethylene glycol (15) tallow polyamine" in the CTFA dictionary; and
(11) Other cationic polymers which can be used in the context of the present invention are polyalkyleneimines, in particular polyethyleneimines, polymers containing vinylpyridine or vinylpyridinium units, condensates of polyamines and of epichlorohydrin, and quaternary polyureylenes.

It is preferable that the cationic polymer be chosen from the following polymers: Polyquaternium-5, such as the product Merquat 5 sold by Calgon;

Polyquaternium-6, such as the product Salcare SC 30 sold by Ciba and the product Merquat 100 sold by Calgon;

Polyquaternium-7, such as the products Merquat S, Merquat 2200 and Merquat 550 sold by Calgon and the product Salcare SC 10 sold by Ciba;

Polyquaternium-10, such as the product Polymer JR400 sold by Amerchol;

Polyquaternium-11, such as the products Gafquat 755, Gafquat 755N and Gafquat 734 sold by ISP;

Polyquaternium-15, such as the product Rohagit KF 720 F sold by Röhm; Polyquaternium-16, such as the products Luviquat FC905, Luviquat FC370, Luviquat HM552 and Luviquat FC550 sold by BASF;

Polyquaternium-22, such as the product Merquat 280 sold by Calgon;

Polyquaternium-28, such as the product Styleze CC10 sold by ISP;

Polyquaternium-39, such as the product Merquat Plus 3330 sold by Calgon;

Polyquaternium-44, such as the product Luviquat Care sold by BASF;

Polyquaternium-46, such as the product Luviquat Hold sold by BASF; and

Polyquaternium-47, such as the product Merquat 2001 sold by Calgon.

The amount of cationic polymer(s) may be from 0.01 to 20% by weight, preferably from 0.05 to 10% by weight, and more preferably from 0.1 to 5% by weight relative to the total weight of the composition according to the present invention.

In another embodiment, the (j) cosmetic active ingredient may be selected from oxidative dyes.

(Oxidative Dye)

The oxidative dye can be selected from oxidation bases and couplers.

The oxidation base can be selected from those conventionally known in oxidation dyeing, preferably from the group consisting of ortho- and para-phenylenediamines, double bases, ortho- and para-aminophenols, heterocyclic bases and the acid addition salts thereof.

There may be mentioned in particular:

(I) the para-phenylenediamines of the following formula (I) and their addition salts with an acid:

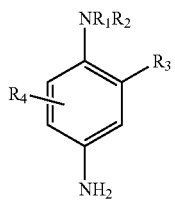

in which:

$R_1$ represents a hydrogen atom, a $C_1$-$C_4$ alkyl radical, a monohydroxy ($C_1$-$C_4$ alkyl) radical, a polyhydroxy-($C_2$-$C_4$ alkyl) radical, a ($C_1$-$C_4$) alkoxy ($C_1$-$C_4$) alkyl radical, a $C_1$-$C_4$ alkyl radical substituted with a nitrogen-containing group, a phenyl radical or a 4'-aminophenyl radical;

$R_2$ represents a hydrogen atom, a $C_1$-$C_4$ alkyl radical, a monohydroxy ($C_1$-$C_4$ alkyl) radical, a polyhydroxy ($C_2$-$C_4$ alkyl) radical, a ($C_1$-$C_4$) alkoxy ($C_1$-$C_4$) alkyl radical or a $C_1$-$C_4$ alkyl radical substituted with a nitrogen-containing group;

$R_1$ and $R_2$ may also form with the nitrogen atom carrying them a 5- or 6-membered nitrogen-containing heterocycle optionally substituted with one or more alkyl, hydroxyl or ureido groups;

$R_3$ represents a hydrogen atom, a halogen atom such as a chlorine atom, a $C_1$-$C_4$ alkyl radical, a sulpho radical, a carboxyl radical, a monohydroxy ($C_1$-$C_4$ alkyl) radical, a hydroxyl ($C_1$-$C_4$ alkoxy) radical, an acetylamino ($C_1$-$C_4$ alkoxy) radical, a mesylamino ($C_1$-$C_4$ alkoxy) radical or a carbamoylamino ($C_1$-$C_4$ alkoxy) radical; and $R_4$ represents a hydrogen or halogen atom or a $C_1$-$C_4$ alkyl radical.

Among the nitrogen-containing groups of formula (I) above, there may be mentioned in particular the amino, mono ($C_1$-$C_4$) alkylamino, ($C_1$-$C_4$) dialkylamino, ($C_1$-$C_4$) trialkylamino, monohydroxy ($C_1$-$C_4$) alkylamino, di(monohydroxy ($C_1$-$C_4$) alkyl)amino, imidazolinium and ammonium radicals.

Among the para-phenylenediamines of formula (I) above, there may be mentioned more particularly para-phenylenediamine, para-tolylenediamine, 2-chloro-paraphenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethylpara-phenylenediamine, N,N-diethyl-para-phenylenediamine, N,N-dipropyl-paraphenylenediamine, 4-amino-N,N-diethyl-3-methylaniline, N,N-bis(β-hydroxyethyl)-paraphenylenediamine, 4-N,N-bis(β-hydroxyethyl)amino-2-methylaniline, 4-N,N-bis(β-hydroxyethypamino-2-chloroaniline, 2-β-hydroxyethyl-para-phenylenediamine, 2-fluoro-paraphenylenediamine, 2-isopropyl-para-phenylenediamine, N-(β-hydroxypropyl)-paraphenylenediamine, 2-hydroxymethyl-para-phenylenediamine, N,N-dimethyl-3-methylpara-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-paraphenylenediamine, 2-β-hydroxyethyloxy-paraphenylenediamine, 2-β-acetylamino-ethyloxy-paraphenylenediamine, N-(β-methoxyethyl)-paraphenylenediamine, 2-methyl-1-N-β-hydroxyethyl-paraphenylenediamine, N-(4-aminophenyl)-3-hydroxypyrrolidine, 2-[{2-[(4-Aminophenyl)amino]ethyl}(2-hydroxyethyl)amino]-ethanol, and their addition salts with an acid.

Among the para-phenylenediamines of formula (I) above, there are most particularly preferred para-phenylenediamine, para-tolylenediamine, 2-isopropyl-paraphenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-paraphenylenediamine, and their addition salts with an acid.

(II) According to the present invention, "double bases" is understood to mean compounds containing at least two aromatic rings on which amino and/or hydroxyl groups are carried.

Among the double bases which can be used as oxidation bases in the dyeing compositions in accordance with the present invention, there may be mentioned in particular compounds corresponding to the following formula (II), and their addition salts with an acid:

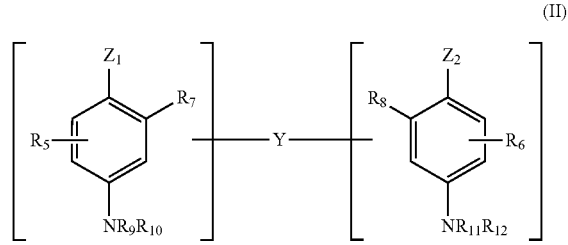

in which:

$Z_1$ and $Z_2$, which are identical or different, represent a hydroxyl or —$NH_2$ radical which may be substituted with a $C_1$-$C_4$ alkyl radical or with a linking arm Y;

the linking arm Y represents a linear or branched alkylene chain comprising from 1 to 14 carbon atoms, which may be interrupted by or which may end with one or more nitrogen-containing groups and/or one or more heteroatoms such as oxygen, sulphur or nitrogen atoms, and optionally substituted with one or more hydroxyl or $C_1$-$C_6$ alkoxy radicals;

$R_5$ and $R_6$ represent a hydrogen or halogen atom, a $C_1$-$C_4$ alkyl radical, a monohydroxy ($C_1$-$C_4$ alkyl) radical, a polyhydroxy ($C_2$-$C_4$ alkyl) radical, an amino ($C_1$-$C_4$ alkyl) radical or a linking arm Y;

$R_7$, $R_8$, $R_9$, $R_{10}$, $R_{11}$ and $R_{12}$, which are identical or different, represent a hydrogen atom, a linking arm Y or a $C_1$-$C_4$ alkyl radical; it being understood that the compounds of formula (II) contain only one linking arm Y per molecule.

Among the nitrogen-containing groups of formula (II) above, there may be mentioned in particular the amino, mono($C_1$-$C_4$)alkylamino, ($C_1$-$C_4$)dialkylamino, ($C_1$-$C_4$)trialkylamino, monohydroxy($C_1$-$C_4$)alkylamino, imidazolinium and ammonium radicals.

Among the double bases of formulae (II) above, there may be mentioned more particularly N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl) tetramethylenediamine, N,N'-bis(4-methylaminophenyl) tetramethylenediamine, N,N'-bis(ethyl)-N,N'-bis(4'-amino-3'-methylphenyl)ethylene-diamine, 1,8-bis(2,5-diaminophenoxy)-3,5-dioxaoctane, and their addition salts with an acid.

Among these double bases of formula (II), N,N'-bis(β-hydroxyethyl)-N,N'-bis(4'-aminophenyl)-1,3-diaminopropanol, 1,8-bis(2,5-diaminophenoxy)-3,5-dioxaoctane or one of their addition salts with an acid are particularly preferred.

(III) The para-aminophenols corresponding to the following formula (III), and their addition salts with an acid:

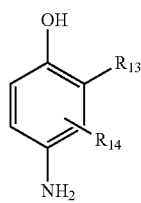

(III)

in which:

$R_{13}$ represents a hydrogen atom, or a halogen atom such as fluorine, a $C_1$-$C_4$ alkyl, monohydroxy($C_1$-$C_4$ alkyl), ($C_1$-$C_4$)alkoxy($C_1$-$C_4$)-alkyl, amino($C_1$-$C_4$ alkyl) or hydroxy($C_1$-$C_4$)alkylamino-($C_1$-$C_4$ alkyl) radical, $R_{14}$ represents a hydrogen atom, or a halogen atom such as fluorine, a $C_1$-$C_4$ alkyl, monohydroxy($C_1$-$C_4$ alkyl), polyhydroxy($C_2$-$C_4$ alkyl), amino($C_1$-$C_4$ alkyl), cyano ($C_1$-$C_4$ alkyl) or ($C_1$-$C_4$)alkoxy($C_1$-$C_4$)alkyl radical.

Among the para-aminophenols of formula (III) above, there may be mentioned more particularly para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and their addition salts with an acid.

(IV) The ortho-aminophenols which can be used as oxidation bases in the context of the present invention are chosen in particular from 2-aminophenol, 2-amino-1-hydroxy-5-methylbenzene, 2-amino-1-hydroxy-6-methylbenzene, 5-acetamido-2-aminophenol, and their addition salts with an acid.

(V) Among the heterocyclic bases which can be used as oxidation bases in the dyeing compositions in accordance with the present invention, there may be mentioned more particularly pyridine derivatives, pyrimidine derivatives, pyrazole derivatives, and their addition salts with an acid.

Among the pyridine derivatives, there may be mentioned more particularly the compounds described for example in GB patents 1,026,978 and 1,153,196, such as 2,5-diaminopyridine, 2-(4-methoxyphenyl)amino-3-aminopyridine, 2,3-diamino-6-methoxypyridine, 2-(β-methoxyethyl) amino-3-amino-6-methoxypyridine, 3,4-diaminopyridine, and their addition salts with an acid.

Among the pyrimidine derivatives, there may be mentioned more particularly the compounds described, for example, in DE patent 2 359 399; JP 88-169571; JP 91-10659 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triamino-pyrimidine, and the pyrazolopyrimidine derivatives such as those mentioned in patent application FR-A-2 750 048 and among which there may be mentioned pyrazolo[1,5-a]-pyrimidine-3,7-diamine; 2,5-dimethyl-pyrazolo[1,5-a]-pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-amino-pyrazolo [1,5-a]pyrimidin-5-ol; 2-(3-amino-pyrazolo-[1,5-a]pyrimidin-7-ylamino)ethanol, 2-(7-aminopyrazolo[1,5-a]pyrimidin-3-ylamino)ethanol, 2-[(3-amino-pyrazolo[1,5-a] pyrimidin-7-yl)-(2-hydroxy-ethyl)amino]-ethanol, 2-[(7-aminopyrazolo[1,5-a]-pyrimidin-3-yl)-(2-hydroxyethy) amino]ethanol, 5,6-dimethylpyrazolo-[1,5-a]pyrimidine-3,7-diamine, 2,6-dimethylpyrazolo-[1,5-a]pyrimidine-3,7-diamine, 2,5,N7,N7-tetramethyl-pyrazolo[1,5-a]pyrimidine-3,7-diamine, 3-amino-5-methyl-7-imidazolylpropyl-aminopyrazolo[1,5-a]-pyrimidine, their addition salts and their tautomeric forms, when a tautomeric equilibrium exists and their addition salts with an acid.

Among the pyrazole derivatives, there may be mentioned more particularly the compounds described in DE patents 3 843 892 and 4 133 957 and patent applications WO 94/08969, WO 94/08970, FR-A-2 733 749 and DE 195 43 988 such as 4,5-diamino-1-methylpyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazino-pyrazole, 1-benzyl-4,5-diamino-3-methyl-pyrazole, 4,5-diamino-3-tert-butyl-1-methylpyrazole, 4,5-diamino-1-tertbutyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxy-methylpyrazole, 4,5-diamino-3-hydroxymethyl-1-methylpyrazole, 4,5-diamino-3-hydroxymethyl-1-isopropyl-pyrazole, 4,5-diamino-3-methyl-1-isopropyl-pyrazole, 4-amino-5-(2'-aminoethyl)amino-1,3-dimethylpyrazole, 3,4,5-triaminopyrazole, 1-methyl-3,4,5-triamino-pyrazole, 3,5- diamino-1-methyl-4-methylaminopyrazole, 3,5-diamino-4-(β-hydroxy-ethyl)amino-1-methylpyrazole, and their addition salts with an acid.

Among the heterocyclic bases which can be used as oxidation bases, there may be mentioned more particularly diaminopyrazolopyrazolones and especially 2,3-diamino-6,7-dihydro-1H5H-[pyrazolo1,2,a]pyrazol-1-one and the addition salts of these diaminopyrazolopyrazolones with an acid.

The couplers may be an oxidation coupler which can be selected from those conventionally known in oxidation dyeing, preferably from the group consisting of meta-phenylenediamines, meta-aminophenols, meta-diphenols, naphthols, heterocyclic couplers and the acid addition salts thereof.

The heterocyclic couplers may be selected from the group consisting of indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines and their addition salts with an acid.

These couplers are more particularly chosen from 2,4-diamino-1-(β-hydroxyethyloxy)benzene, 2-methyl-5-aminophenol, 5-N-(β-hydroxyethyl)amino-2-methylphenol, 3-aminophenol, 2-chloro-3-amino-6-methylphenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 2-methyl-5-hydroxyethylaminophenol, 4-amino-2-hydroxytoluene, 1,3-bis(2,4-diaminophenoxy)-propane, sesamol, 1-amino-2-methoxy-4,5-methylene-dioxybenzene, α-naphthol, 6-hydroxyindole, 4-hydroxyindole, 4-hydroxy-N-methylindole, 6-hydroxy-indoline, 2,6-dihydroxy-4-methylpyridine, 1-H-3-methylpyrazol-5-one, 1-phenyl-3-methylpyrazol-5-one, 2-amino-3-hydroxypyridine, 3,6-dimethyl-pyrazolo[3,2-c]-1,2,4-triazole, 2,6-dimethylpyrazolo[1,5-b]-1,2,4-triazole and their addition salts with an acid.

In general, the addition acid salts of the oxidation bases and couplers are chosen in particular from hydrochlorides, hydrobromides, sulfates, citrates, succinates, tartrates, lactates, tosylates, benzenesulfonates, phosphates and acetates.

The amount of the oxidative dye(s) (oxidation base(s) and/or coupler(s)) may be in an amount of 0.001% by weight or more, and may contain, for example, from 0.001 to 20% by weight, preferably from 0.01 to 10% by weight, and more preferably from 0.1 to 5% by weight, relative to the total weight of the composition to be prepared by the process according to the present invention.

In another embodiment, the (j) cosmetic active ingredient may be an additional alkaline agent.

(Additional Alkaline Agent)

The additional alkaline agent may be an inorganic alkaline agent other than the above ingredient (f). It is preferable that the inorganic alkaline agent be selected from the group consisting of alkaline metal hydroxides; alkaline earth metal hydroxides; alkaline metal phosphates and monohydrogenophosphates such as sodium phosphate or sodium monohydrogeno phosphate.

As examples of the inorganic alkaline metal hydroxides, mention may be made of sodium hydroxide and potassium hydroxide. As examples of the alkaline earth metal hydroxides, mention may be made of calcium hydroxide and magnesium hydroxide. As the inorganic alkaline agent, sodium hydroxide may be preferable.

The alkaline agent may be an organic alkaline agent other than the above ingredient (f). It is preferable that the organic alkaline agent be selected from the group consisting of monoamines and derivatives thereof; diamines and derivatives thereof; polyamines and derivatives thereof; basic amino acids and derivatives thereof; oligomers of basic amino acids and derivatives thereof; polymers of basic amino acids and derivatives thereof; urea and derivatives thereof; and guanidine and derivatives thereof.

As examples of the organic alkaline agents, mention may be made of alkanolamines such as mono-, di- and tri-ethanolamine, and isopropanolamine; urea, guanidine and their derivatives; basic amino acids such as lysine, ornithine or arginine; and diamines such as those described in the structure below:

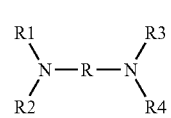

wherein

R denotes an alkylene such as propylene optionally substituted by a hydroxyl or a $C_1$-$C_4$ alkyl radical, and $R_1$, $R_2$, $R_3$ and $R_4$ independently denote a hydrogen atom, an alkyl radical or a $C_1$-$C_4$ hydroxyalkyl radical, which may be exemplified by 1,3-propanediamine and derivatives thereof. Arginine, urea and monoethanolamine are preferable.

The amount of the additional alkaline agent(s) may range from 0.1 to 15% by weight, preferably from 1 to 20% by weight, more preferably from 1 to 5% by weight, relative to the total weight of the composition according to the present invention. It may be preferable that the amount of the additional alkaline agent(s) be 4% by weight or less, more preferably 2% by weight or less, and even more preferably 1% by weight or less. Most preferably, the composition according to the present invention comprises no additional alkaline agent.

(Other Optional Ingredients)

The composition according to the present invention may also comprise an effective amount of other ingredients, for example, which are common in cosmetic compositions, such as pH adjusters, various common adjuvants, vitamins such as Vitamin C, anti-ageing agents, whitening agents, anti-greasy skin agents, chelating agents such as EDTA and pentasodium pentetate, UV screening agents, anti-oxidating agents such as Vitamin C and sodium metabisulfite, preserving agents such as phenoxyethanol, provitamins, for instance, panthenol, opacifiers, fragrances, plant extracts, direct dyes, and so on.

As the pH adjusters, mention may be made of an acidifying agent such as mineral or organic acids, for instance hydrochloric acid, orthophosphoric acid, carboxylic acids, for instance tartaric acid, citric acid, lactic acid, or sulphonic acids.

The composition according to the present invention may further comprise at least one organic solvent. Therefore, the organic solvent is preferably water-miscible or water-soluble. As the organic solvent, there may be mentioned, for example, $C_1$-$C_4$ alkanols, such as ethanol and isopropanol; aromatic alcohols such as benzyl alcohol and phenoxyethanol; analogous products; and mixtures thereof.

The organic solvent(s) may be present in an amount ranging from less than 20% by weight, preferably from 15% by weight or less, and more preferably from 10% by weight or less, relative to the total weight of the composition. The amount of the organic solvent(s) in the composition according to the present invention may be 0.01% by weight or more, preferably 0.1% by weight or more, and more preferably 1% by weight or more, relative to the total weight of the composition. Thus, it is possible that the amount of the organic solvent(s) may range from 0.01 to 20% by weight, preferably from 0.1 to 15% by weight, and more preferably from 1 to 10% by weight, relative to the total weight of the composition.

(Emulsion)

The composition according to the present invention is in the form of an O/W emulsion.

The particle size of the oil droplets may be 10 μm or less, preferably 5 μm or less, and more preferably 3 μm or less. The particle size of the oil droplet may be 10 nm or more, preferably 20 nm or more, and even more preferably 30 nm or more. Thus, it is possible that the oil droplets have a particle size of from 10 nm to 10 μm, preferably from 20 nm to 5 μm, and more preferably from 30 nm to 3 μm.

The composition according to the present invention may include so-called α-gel structure around the droplet of the (b) oil in the aqueous phase thereof. The α-gel structure may be formed by layers composed of the (a) fatty alcohol, the (c) nonionic surfactant having an HLB value of 15 or more and the (d) nonionic surfactant having an HLB value of 5 or less. The water between the above layers can trap the (f) alkaline agent or ammonia.

[Preparation Process]

The composition according to the present invention can be prepared by a process comprising the steps of:

(1) mixing (a) at least one fatty alcohol, (b) at least one oil, (c) at least one nonionic surfactant having an HLB value of 15 or more, (d) at least one nonionic surfactant having an HLB value of 5 or less, (e) at least one diol having a straight chain of four or more consecutive carbon atoms, and water;

(2) adding water to the mixture obtained by step (1) to prepare an oil-in-water [O/W] emulsion; and (3) adding (f) at least one inorganic alkaline agent to the O/W emulsion obtained by step (2).

The process for preparing the composition according to the present invention is based on so-called D-phase emulsification.

Each step in the process according to the present invention will be explained below.

Step (1) is preparing a mixture, preferably an emulsion, more preferably an oil-in-detergent [O/D] emulsion, or preferably a gel emulsion, by mixing (a) at least one fatty alcohol, (b) at least one oil, (c) at least one nonionic surfactant having an HLB value of 15 or more, (d) at least one nonionic surfactant having an HLB value of 5 or less, (e) at least one diol having a straight chain of four or more consecutive carbon atoms, and water. The continuous phase in the emulsion or the gel emulsion includes the ingredients (c), (d), (e) and water. Gel emulsion is an emulsion which is viscoelastic and sometimes transparent or translucent, and therefore looks like a gel.

It is preferable that the above ingredients (a) to (e) be previously mixed before mixing with water.

The amount of water used in step (1) is a relatively small portion of the total amount of water to be included in the composition according to the present invention. The amount of the water used in step (1) may be from 0.01 to 20% by weight, preferably from 0.1 to 15% by weight, and more preferably from 1 to 10% by weight, of the total weight of the water to be included in the composition according to the present invention.

Step (1) may be performed at a temperature ranging from room temperature (25° C.) to an elevated temperature such as from 50 to 90° C., preferably from 60 to 85° C., and more preferably from 70 to 80° C.

The temperature of the ingredients (a) to (e) as well as the water used in step (1) may be controlled at a temperature ranging from room temperature (25° C.) to an elevated temperature such as from 50 to 90° C., preferably from 60 to 85° C., and more preferably from 70 to 80° C.

It is preferable that the obtained mixture, preferably an emulsion, and more preferably an oil-in-detergent [O/D] emulsion, be in the form of a transparent and viscous liquid such as a gel.

Step (2) is adding water to the mixture, preferably an emulsion or gel, obtained by step (1) to prepare an oil-in-water [O/W] emulsion.

The continuous phase in the emulsion, preferably an oil-in-detergent [O/D] emulsion, or a gel emulsion is replaced with water in step (2) to form an O/W emulsion. The O/W emulsion may be in the form of a translucent liquid or paste such as a cream.

The amount of water used in step (2) is a large portion of the water to be included in the composition to be prepared by the process according to the present invention. For example, the water used in step (2) can be the water remaining after subtracting the amount of water used in step (1) from the total amount of water to be included in the composition to be prepared by the process according to the present invention. The amount of the water used in step (2) may be from 80 to 99.99% by weight, preferably from 85 to 99.9% by weight, and more preferably from 90 to 99% by weight, of the total weight of the water to be included in the composition according to the present invention.

Step (2) may be performed at a temperature ranging from room temperature (25° C.) to an elevated temperature such as from 50 to 90° C., preferably from 60 to 85° C., and more preferably from 70 to 80° C.

The temperature of the water used in step (2) may be controlled at a temperature ranging from room temperature (25° C.) to an elevated temperature such as from 50 to 90° C., preferably from 60 to 85° C., and more preferably from 70 to 80° C.

Step (3) is adding the above ingredient (f) to the O/W emulsion obtained by step (2). The ingredient (f) can provide the O/W emulsion from step (2) with the ability to provide a cosmetic effect such as bleaching or coloring to, for example, keratin fibers such as hair.

It is preferable that the mixture or emulsion be homogenized by mixing, stirring or agitating in steps (1) to (3) to make the mixture or emulsion uniform.

The D-phase emulsification can prepare an O/W emulsion including a very fine dispersed phase, i.e., oil droplets. Thus, a composition in the form of an O/W emulsion including very fine oil droplets can be produced by the above process according to the present invention.

Steps (1) to (3) can be performed with normal or conventional equipment for preparing emulsions. Thus, no special equipment is necessary for performing the process according to the present invention. Therefore, the process according to the present invention can be performed economically.

[Cosmetic Use]

It is preferable that the composition according to the present invention be a cosmetic composition for keratin fibers, preferably hair, in order to color or bleach the keratin fibers.

Thus, one aspect of the present invention is the use of the composition explained above for cosmetic treatment of keratin fibers such as hair, in particular coloring or bleaching the keratin fibers.

It is preferable that the composition according to the present invention have a viscosity at 25° C. of from 3,000 to 30,000 mPa·s, more preferably from 3,500 to 20,000 mPa·s, and even more preferably from 4,000 to 15,000 mPa·s. Due to the appropriate viscosity, the composition according to the present invention is easy to handle. Therefore, the composition according to the present invention has no or reduced difficulty in self-handling (e.g., when mixing with an oxidizing composition explained below) by users of the composition.

In one embodiment for the cosmetic treatment of keratin fibers such as hair, the composition according to the present invention can be mixed with an oxidizing composition.

(Oxidizing Composition)

The oxidizing composition comprises at least one oxidizing agent.

The oxidizing agent may be chosen from hydrogen peroxide, peroxygenated salts, and compounds capable of producing hydrogen peroxide by hydrolysis. For example, the oxidizing agent can be chosen from hydrogen peroxide, urea peroxide, alkali metal bromates and ferricyanides and per-salts such as perborates and persulphates. At least one oxidase enzyme chosen, for example, from laccases, peroxidases and 2-electron oxidoreductases such as uricase may also be used as the oxidizing agent, where appropriate in the presence of the respective donor or co-factor thereof.

In one embodiment, the oxidizing agent is hydrogen peroxide, and the oxidizing composition is an aqueous hydrogen peroxide solution.

The hydrogen peroxide concentration may range from 0.15 to 12% by weight such as from 0.6 to 9% by weight relative to the total weight of the oxidizing composition. The concentration of compounds capable of forming hydrogen peroxide by hydrolysis may range from 0.1 to 25% by weight relative to the total weight of the oxidizing composition.

In one embodiment, when the oxidizing composition is an aqueous hydrogen peroxide solution, the oxidizing composition may contain at least one hydrogen peroxide stabilizer, which may be chosen, for example, from alkali metal and alkaline-earth metal pyrophosphates, alkali metal and alkaline-earth metal stannates, phenacetin and salts of acids and of oxyquinoline, for example, oxyquinoline sulphate. In another embodiment, at least one stannate optionally in combination with at least one pyrophosphate is used.

It is also possible to use salicylic acid and its salts, pyridinedicarboxylic acid and its salts, and paracetamol.

In the oxidizing composition, the concentration of the hydrogen peroxide stabilizer(s) may range from 0.0001 to 5% by weight such as from 0.01 to 2% by weight relative to the total weight of the oxidizing composition.

In the oxidizing composition comprising hydrogen peroxide, the concentration ratio of the hydrogen peroxide to the at least one stabilizer may range from 0.05:1 to 1,000:1, such as from 0.1:1 to 500:1 and further such as from 1:1 to 200:1.

In another embodiment for the cosmetic treatment of keratin fibers such as hair, the oxidizing agent may be present in the composition according to the present invention as the (j) cosmetic active ingredient (ready-to-use composition).

If the oxidizing agent is present in the composition according to the present invention, the amount of the oxidizing agent(s) may range from 0.0001 to 10% by weight, preferably from 0.001 to 10% by weight, and more preferably from 0.01 to 5% by weight, relative to the total weight of the composition according to the present invention.

In this embodiment, the composition according to the present invention is in the form of a so-called "ready-to-use" composition.

In one embodiment for the cosmetic treatment of keratin fibers such as hair, the composition according to the present invention can be used in treating (e.g., coloring or bleaching) the keratin fibers, in accordance with the following steps of:

applying to wet or dry keratin fibers a mixture which is either prepared extemporaneously by mixing, just before the application to the keratin fibers, the composition according to the present invention and an oxidizing composition, or a composition according to the present invention which is in the form of a "ready-to-use" composition including the oxidizing agent as explained above;

leaving the mixture or composition to act for an exposure time, such as ranging from 1 to 60 minutes approximately, and further such as from 5 to 45 minutes approximately; rinsing the fibers; and optionally washing them with shampoo, rinsing them again and then drying them.

The application of the mixture or composition may be realized at room temperature or with the use of a warming device which is able to produce a temperature ranging from 40 to 220° C., preferably ranging from 40 to 80° C.

The cosmetic treatments explained above can provide keratin fibers such as hair with superior cosmetic effects such as good (intense) coloring or bleaching effects, as well as a good feeling to the touch of the keratin fibers, while controlling malodor due to the ammonia ingredient in the mixture or composition.

EXAMPLES

The present invention will be described in a more detailed manner by way of examples. However, these examples should not be construed as limiting the scope of the present invention.

Examples 1-8 and Comparative Examples 1-4

(Preparation)

The following compositions according to Examples (Ex.) 1-8 and Comparative Examples (Comp. Ex.) 1-4, shown in Tables 1 and 2, were prepared by mixing the components shown in Tables 1 and 2 as follows.

Step 1: The ingredients of fatty alcohol, oil, surfactant and polyol shown in Tables 1 and 2 were mixed in a container and heated at 80° C. Once all materials were dissolved, preheated water in an amount of 5% by weight relative to the total weight of the composition was added into the mixture under mild agitation at 80° C. Thus, an opaque mixture was transformed into a transparent liquid.

Step 2: Next, the remaining water was added into the mixture and emulsified at 80° C. for 10 minutes. Then, the mixture was cooled down to a temperature below 40° C. The stabilizer and cationic polymer ingredients were pre-dissolved in water and added into the mixture above. Finally, the alkali ingredient(s) was/were put in the mixture and stirred to homogenize the mixture.

The numerical values for the amounts of the components shown in Tables 1 and 2 are based on "% by weight". The "ammonia" and "polyquaternium-6" in Tables 1 and 2 are aqueous ammonia including 25% by weight of ammonia, and an aqueous solution including 40% by weight of polyquaternium-6, respectively.

(Evaluation 1)

The mixability, pungent odor, and hair lightening effect of the obtained O/W emulsions according to Examples 1-8 and Comparative Examples 1-4 were measured and evaluated as follows. The composition of Developer (A) is as follows.

Developer (A)

|  | Concentration (wt %) |
|---|---|
| Liquid paraffin | 0.80 |
| Stearyl alcohol | 0.70 |
| Cetyl alcohol | 0.70 |
| Myristyl alcohol | 2.80 |
| Ceteareth-33 | 1.70 |
| Beheneth-10 | 0.50 |
| Cocamidopropyl betaine | 0.143 |
| Polyquaternium-6 | 0.50 |
| 35% Hydrogen peroxide | 11.7 |
| Phosphoric acid | q.s. |
| Water | q.s. 100 |

The results are shown in Table 3.

(1) Mixability

Each of the compositions according to Examples 1-8 and Comparative Examples 1-4 were mixed with Developer (A) at a mixing weight ratio of 1:1, by stirring the mixture with a blush in a container for 30 seconds and the behavior and aspect of the mixture was evaluated based on visual observation under the following criteria.

| Very Good | The mixture became a smooth and homogeneous cream |
| Good | The mixture became an inhomogeneous cream |
| Poor | The mixture included grains after mixing |

(2) Pungent Odor

Each of the compositions according to Examples 1-8 and Comparative Examples 1-4 were mixed with Developer (A) at a mixing weight ratio of 1:1, and the pungent odor at 10 cm above the mixture was scored by eight panelists on a five-point scale under the following criteria.

| 1 | Very Weak |
| 2 | Slight |
| 3 | Moderate |
| 4 | Strong |
| 5 | Very Strong |

The mixture was evaluated by the average score of eight panelists under the following criteria.

| Very Good | Average score was less than 2 |
| Good | Average score was from 2 to less than 3 |
| Fair | Average score was from 3 to less than 4 |
| Poor | Average score was 4 or more |

(3) Hair Lightening (Bleaching) Effect

Each of the compositions according to Examples 1-8 and Comparative Examples 1-4 was mixed with Developer (A) at a mixing weight ratio of 1:1. 5 g of the mixture thus obtained was applied onto 1 g of a Japanese hair mesh.

After leaving the hair mesh for 30 minutes at 27° C., the hair mesh was rinsed, shampooed, and dried. The color of each of the original undyed hair mesh and the dyed hair mesh was measured by a KONICA MINOLTA SPECTROPHOTOMETER CM-3600d, and the change in the color ($\Delta E^*ab$) between the original undyed hair mesh and the dyed hair mesh was evaluated under the following criteria.

| Good | $\Delta E^*ab$ is more than 8.0 |
| Fair | $\Delta E^*ab$ is from 5 to 8.0 |
| Poor | $\Delta E^*ab$ is less than 5.0 |

TABLE 1

|  | Ingredient | Ex. 1 | Ex. 2 | Ex. 3 | Ex. 4 | Ex. 5 | Ex. 6 | Ex. 7 | Ex. 8 |
|---|---|---|---|---|---|---|---|---|---|
| FA | Cetearyl alcohol | 10.00 | 10.00 | 10.00 | 10.00 | 10.00 | 10.00 | 10.00 | 10.00 |
| O | Mineral oil | 10.00 | 10.00 | 10.00 | 10.00 | 10.00 | 10.00 | 10.00 | 10.00 |
| NS | Ceteareth-33 (HLB: 18) | 2.00 | 2.00 | — | — | — | — | 2.00 | 2.00 |
|  | Laureth-23 (HLB: 16.9) | — | — | — | — | — | 2.00 | — | — |
|  | Oleth-30 (HLB: 16.6) | — | — | — | — | 2.00 | — | — | — |
|  | Ceteareth-25 (HLB: 16.2) | — | — | — | 2.0 | — | — | — | — |
|  | Steareth-20 (HLB: 15.3) | 2.00 | 2.00 | 3.00 | 2.00 | 2.00 | 2.00 | 2.00 | 2.00 |
|  | Steareth-2 (HLB: 4.8) | — | 2.00 | — | — | — | — | — | — |
|  | Glyceryl stearate (HLB: 3.8) | 2.00 | — | 3.00 | 2.00 | 2.00 | 2.00 | 2.00 | 2.00 |
| AS | Stearic acid | — | — | — | — | — | — | 0.4 | — |
|  | Dicetyl phosphate | — | — | — | — | — | — | 0.014 | — |
|  | Ceteth-10 phosphate | — | — | — | — | — | — | 0.011 | — |
| CS | Behentrimonium chloride (79%) | — | — | — | — | — | — | — | 0.5 |
| P | Glycerin | 5.00 | 5.00 | 5.00 | 5.00 | 5.00 | 5.00 | 5.00 | 5.00 |
|  | Butyleneglycol | 5.00 | 5.00 | 5.00 | 5.00 | 5.00 | 5.00 | 5.00 | 5.00 |
| S | EDTA | 0.20 | 0.20 | 0.20 | 0.20 | 0.20 | 0.20 | 0.20 | 0.20 |
|  | Ascorbic acid | 0.50 | 0.50 | 0.50 | 0.50 | 0.50 | 0.50 | 0.50 | 0.50 |
|  | Sodium metabisulfite | 0.50 | 0.50 | 0.50 | 0.50 | 0.50 | 0.50 | 0.50 | 0.50 |
| CP | Polyquaternium-6 (40%) | 0.50 | 0.50 | 0.50 | 0.50 | 0.50 | 0.50 | 0.50 | 0.50 |

TABLE 1-continued

|   | Ingredient | Ex. 1 | Ex. 2 | Ex. 3 | Ex. 4 | Ex. 5 | Ex. 6 | Ex. 7 | Ex. 8 |
|---|---|---|---|---|---|---|---|---|---|
| A | Ammonium bicarbonate | — | — | — | 2.00 | 2.00 | 2.00 | — | — |
|   | Ammonia (25%) | 7.20 | 7.20 | 7.20 | 7.20 | 7.20 | 7.20 | 7.20 | 7.20 |
|   | Water | q.s. 100 | q.s. 100 | q.s. 100 | q.s. 100 | q.s. 100 | q.s. 100 | q.s. 100 | q.s. 100 |

FA: Fatty Alcohol
O: Oil
NS: Nonionic Surfactant
AS: Anionic Surfactant
CS: Cationic Surfactant
P: Polyol
S: Stabilizer
CP: Cationic Polymer
A: Alkali

TABLE 2

|   | Ingredient | Comp. Ex. 1 | Comp. Ex. 2 | Comp. Ex. 3 | Comp. Ex. 4 |
|---|---|---|---|---|---|
| FA | Cetearyl alcohol | 10.00 | 10.00 | 10.00 | 10.00 |
| O | Mineral oil | 10.00 | 10.00 | 10.00 | 10.00 |
| NS | Ceteareth-33 (HLB: 18) | 3.00 | 2.00 | 2.00 | 2.00 |
|   | Steareth-20 (HLB: 15.3) | 3.00 | 2.00 | 2.00 | 2.00 |
|   | Glyceryl stearate (HLB: 3.8) | — | 2.00 | 2.00 | 2.00 |
| P | Glycerin | 5.00 | — | — | 5.00 |
|   | Butyleneglycol | 5.00 | — | — | 5.00 |
|   | Propyleneglycol | — | 10.00 | — | — |
| S | EDTA | 0.20 | 0.20 | 0.20 | 0.20 |
|   | Ascorbic acid | 0.50 | 0.50 | 0.50 | 0.50 |
|   | Sodium metabisulfite | 0.50 | 0.50 | 0.50 | 0.50 |
| CP | Polyquaternium-6 (40%) | 0.50 | 0.50 | 0.50 | 0.50 |
| A | Ammonium bicarbonate | — | — | — | 2.00 |
|   | Monoethanolamine | — | — | — | 4.00 |
|   | Ammonia (25%) | 7.20 | 7.20 | 7.20 | — |
|   | Water | q.s. 100 | q.s. 100 | q.s. 100 | q.s. 100 |

FA: Fatty Alcohol
O: Oil
NS: Nonionic Surfactant
AS: Anionic Surfactant
CS: Cationic Surfactant
P: Polyol
S: Stabilizer
CP: Cationic Polymer
A: Alkali (Evaluation 2)

(4) Hair Conditioning Effect

Each of the compositions according to Examples 1-8 and Comparative Examples 1-4 was mixed with Developer (A) at a mixing weight ratio of 1:1. 10 g of the mixture thus obtained was applied onto 3 g of a Japanese hair mesh.

After leaving the hair mesh for 30 minutes at 27° C., the hair mesh was rinsed, shampooed, and dried. Then, the feeling to the touch of the hair mesh was evaluated by 5 trained panelists.

Four or five panelists answered that the feeling to the touch of the hair for Examples 1-8 was good.

(5) Hair Coloring Effect

The composition according to Example 9 in Table 4 shown below was mixed with Developer (A) at a mixing weight ratio of 1:1. The numerical values for the amounts of the ingredients shown in Table 4 are based on "% by weight". The "ammonia" and "polyquaternium-6" in Table 4 are aqueous ammonia including 25% by weight of ammonia, and an aqueous solution including 40% by weight of polyquaternium-6, respectively.

TABLE 3

|   | Ex. 1 | Ex. 2 | Ex. 3 | Ex. 4 | Ex. 5 | Ex. 6 | Ex. 7 | Ex. 8 |
|---|---|---|---|---|---|---|---|---|
| Mixability | Very Good | Very Good | Very Good | Very Good | Very Good | Very Good | Very Good | Very Good |
| Pungent Odor | Very Good | Very Good | Very Good | Good | Good | Good | Very Good | Good |
| Hair Lightening Effect | Good | Good | Good | Good | Good | Good | Good | Good |

|   | Comp. Ex. 1 | Comp. Ex. 2 | Comp. Ex. 3 | Comp. Ex. 4 |
|---|---|---|---|---|
| Mixability | Very Good | Poor | Very Good | Very Good |
| Pungent Odor | Poor | Fair | Fair | Good |
| Hair Lightening Effect | Good | Good | Good | Poor |

It is clear from Tables 1-3 that the compositions according to the present invention have superior usability, less odor and better hair lightening effects, due to the combination of a nonionic surfactant with an HLB value of 15 or more, a nonionic surfactant with an HLB value of 5 or less, a specific diol, and an inorganic alkaline agent, in the presence of a fatty alcohol and oil, as compared to the compositions which lack the element of the combination.

100 g of the mixture thus obtained was applied onto the hair of 3 model heads including more than 50% of gray hair.

After leaving the hair for 30 minutes, the model's hair was rinsed, shampooed, and dried. The coverage level of the gray hair was scored by trained panelists on an 8-point score system (score of 1: not covered-score of 8: totally covered).

The average score of the 3 model heads was 7.3. Thus, the composition according to Example 9 was found to provide very good hair coloring performance.

TABLE 4

| | Ingredient | Ex. 9 |
|---|---|---|
| FA | Cetearyl alcohol | 10.00 |
| O | Mineral oil | 10.00 |
| NS | Ceteareth-33 | 2.00 |
| | Steareth-20 | 2.00 |
| | Glyceryl stearate | 2.00 |
| P | Glycerin | 5.00 |
| | Butyleneglycol | 5.00 |
| S | EDTA | 0.20 |
| | Ascorbic acid | 0.50 |
| | Sodium metabisulfite | 0.50 |
| D | p-Aminophenol (and) sodium metabisulfite | 0.14 |
| | Resorcinol | 0.29 |
| | m-Aminophenol | 0.065 |
| | Toluene-2,5-diamine (and) thioglycerin | 0.22 |
| CP | Polyquaternium-6 (40%) | 0.50 |
| A | Ammonia (25%) | 8.00 |
| | Water | q.s. 100 |

FA: Fatty Alcohol
O: Oil
NS: Nonionic Surfactant
P: Polyol
S: Stabilizer
D: Dye
CP: Cationic Polymer
A: Alkali It is clear from the above test results that the composition according to the present invention can provide keratin fibers such as hair with a good feeling to the touch and good coloring performance.

The invention claimed is:

1. A composition, in the form of an O/W emulsion, comprising:
   (a) at least one fatty alcohol;
   (b) at least one oil selected from hydrocarbon oils or mineral oil;
   (c) at least one nonionic surfactant having an HLB value of about 15 or more;
   (d) at least one nonionic surfactant having an HLB value of about 5 or less;
   (e) at least one $C_4$-$C_8$ diol, wherein the amount of the diol ranges from about 3% to about 10% by weight, relative to the total weight of the composition;
   (f) at least one alkaline agent selected from the group consisting of ammonia, ammonium hydroxide, ammonium salts, or mixtures thereof; and
   (g) water.

2. The composition according to claim 1, wherein the (a) fatty alcohol is selected from straight or branched, unsaturated $C_{6-30}$ alcohols; straight or branched, saturated $C_{6-30}$ alcohols; or straight or branched, saturated $C_{12-20}$ alcohols.

3. The composition according to claim 1, wherein the amount of the (a) fatty alcohol ranges from about 0.5% to about 30% by weight, relative to the total weight of the composition.

4. The composition according to claim 1, wherein the amount of the (b) oil ranges from about 0.5% to about 30% by weight, relative to the total weight of the composition.

5. The composition according to claim 1, wherein the (c) nonionic surfactant having an HLB value of about 15 or more is selected from oxyethylenated fatty alcohols comprising more than 10 oxyethylene units, oxyethylenated fatty alcohols comprising more than 15 oxyethylene units, or oxyethylenated fatty alcohols comprising more than 20 oxyethylene units.

6. The composition according to claim 1, wherein the amount of the (c) nonionic surfactant having an HLB value of about 15 or more ranges from about 0.1% to about 15% by weight, relative to the total weight of the composition.

7. The composition according to claim 1, wherein the amount of the (c) nonionic surfactant having an HLB value of about 15 or more ranges from about 1% to about 5% by weight, relative to the total weight of the composition.

8. The composition according to claim 1, wherein the (d) nonionic surfactant having an HLB value of about 5 or less is selected from fatty acid esters of glycerol.

9. The composition according to claim 1, wherein the amount of the (d) nonionic surfactant having an HLB value of about 5 or less ranges from about 0.1% to about 15% by weight, relative to the total weight of the composition.

10. The composition according to claim 1, wherein the amount of the (d) nonionic surfactant having an HLB value of about 5 or less ranges from about 1% to about 5% by weight, relative to the total weight of the composition.

11. The composition according to claim 1, wherein the (e) $C_4$-$C_8$ diol is selected from the group consisting of butylene glycol, dibutyleneglycol, or mixtures thereof.

12. The composition according to claim 1, wherein the amount of the (f) alkaline agent ranges from about 0.1% to about 10% by weight, relative to the total weight of the composition.

13. The composition according to claim 1, wherein the amount of the (f) alkaline agent ranges from about 1% to about 5% by weight, relative to the total weight of the composition.

14. The composition according to claim 1, wherein the weight ratio of the amount of (a) fatty alcohol to the amount of (b) oil ranges from about 5:1 to about 1:5.

15. The composition according to claim 1, wherein the weight ratio of the amount of (a) fatty alcohol to the amount of (b) oil ranges from about 2:1 to about 1:2.

16. A cosmetic composition in the form of an O/W emulsion for coloring or bleaching keratin fibers, the composition comprising:
   (a) at least one fatty alcohol;
   (b) at least one oil selected from hydrocarbon oils or mineral oil;
   (c) at least one nonionic surfactant having an HLB value of about 15 or more;
   (d) at least one nonionic surfactant having an HLB value of about 5 or less;
   (e) at least one $C_4$-$C_8$ diol, wherein the amount of the diol ranges from about 3% to about 10% by weight, relative to the total weight of the composition;
   (f) at least one alkaline agent selected from the group consisting of ammonia, ammonium hydroxide, ammonium salts, or mixtures thereof; and
   (g) water.

17. A process for preparing a composition, the process comprising:
   (1) mixing (a) at least one fatty alcohol, (b) at least one oil selected from hydrocarbon oils or mineral oil, (c) at least one nonionic surfactant having an HLB value of about 15 or more, (d) at least one nonionic surfactant having an HLB value of about 5 or less, (e) at least one $C_4$-$C_8$ diol, wherein the amount of the diol ranges from about 3% to about 10% by weight, relative to the total weight of the composition, and water;
   (2) adding water to the mixture obtained by step (1) to prepare an 01W emulsion; and
   (3) adding (f) at least one inorganic alkaline agent to the O/W emulsion obtained by step (2), wherein the alkaline agent is selected from the group consisting of ammonia, ammonium hydroxide, ammonium salts, or mixtures thereof.

\* \* \* \* \*